US012801766B2

(12) United States Patent
Warneck

(10) Patent No.: US 12,801,766 B2
(45) Date of Patent: Nov. 17, 2026

(54) INTEGRATED PLATFORM AND NETWORK FOR VIRTUAL HEALTH

(71) Applicant: Journey Health Solutions, Inc., Lexington, MA (US)

(72) Inventor: Melissa Allison Warneck, Lexington, MA (US)

(73) Assignee: Journey Health Solutions, Inc., Lexington, MA (US)

( * ) Notice: Subject to any disclaimer, the term of this patent is extended or adjusted under 35 U.S.C. 154(b) by 0 days.

(21) Appl. No.: 19/295,337

(22) Filed: Aug. 8, 2025

(65) Prior Publication Data

US 2026/0141096 A1 May 21, 2026

Related U.S. Application Data

(60) Provisional application No. 63/681,216, filed on Aug. 9, 2024.

(51) Int. Cl.
*G06F 21/62* (2013.01)
*G06F 16/35* (2025.01)
*G06F 21/30* (2013.01)
*G16H 10/60* (2018.01)

(52) U.S. Cl.
CPC .......... *G06F 21/6209* (2013.01); *G06F 16/35* (2019.01); *G06F 21/30* (2013.01); *G16H 10/60* (2018.01); *G06F 2221/2113* (2013.01); *G06F 2221/2141* (2013.01)

(58) Field of Classification Search
CPC ...... G06F 21/6209; G06F 16/35; G06F 21/30; G06F 2221/2113; G06F 2221/2141; G16H 10/60
See application file for complete search history.

(56) References Cited

U.S. PATENT DOCUMENTS

| | | | | |
|---|---|---|---|---|
| 7,949,546 B1 * | 5/2011 | Klieman | G16H 10/60 600/300 |
| 11,664,099 B1 * | 5/2023 | Jain | G16H 40/67 705/2 |
| 2010/0179831 A1 | 7/2010 | Brown et al. | |
| 2011/0112862 A1 * | 5/2011 | Yu | G06F 16/958 707/707 |
| 2014/0180719 A1 | 6/2014 | Bell et al. | |

(Continued)

FOREIGN PATENT DOCUMENTS

| | | |
|---|---|---|
| JP | 2020089740 A | 6/2020 |
| WO | 0163538 A1 | 8/2001 |

OTHER PUBLICATIONS

International Search Report and Written Opinion issued in PCT/US2025/041345 on Apr. 11, 2025.

*Primary Examiner* — Sm A Rahman
(74) *Attorney, Agent, or Firm* — Goodwin Procter LLP

(57) ABSTRACT

A method for providing a virtual health platform including receiving health data associated with a first user, assigning at least one data category to the health data, storing the health data in a database, receiving, from a second user, a request to access the health data, identifying a permission tier associated with the at least one data category assigned to the health data, and determining whether the second user has permission to access the health data based on the identified permission tier and an identity of the second user.

26 Claims, 12 Drawing Sheets

(56) References Cited

U.S. PATENT DOCUMENTS

| | | | | |
|---|---|---|---|---|
| 2015/0046183 | A1* | 2/2015 | Cireddu | G16H 40/67 705/3 |
| 2016/0283661 | A1* | 9/2016 | Zwinger | G06F 21/602 |
| 2018/0137247 | A1* | 5/2018 | Bore | G16H 80/00 |
| 2019/0019574 | A1* | 1/2019 | Byrnes | G16H 10/60 |
| 2024/0220324 | A1* | 7/2024 | Talavera | G06F 9/4401 |

* cited by examiner

INTEGRATED PLATFORM AND NETWORK FOR VIRTUAL HEALTH

CROSS REFERENCE TO RELATED APPLICATIONS

This application claims priority to U.S. Provisional Patent Application No. 63/681,216, filed on Aug. 9, 2024 and titled "INTEGRATED PLATFORM AND NETWORK FOR VIRTUAL HEALTH," the entire disclosure of which is hereby incorporated by reference.

TECHNICAL FIELD

This specification relates to virtual health and personal data platforms and, in particular, to virtual platforms that provision health and/or personal data, regulate access to health and/or personal data, and authenticate users associated with health and/or personal data.

BACKGROUND

Health or medical data is typically stored using a combination of electronic and physical records. Most modern healthcare facilities use Electronic Health Records (EHRs) systems to store patient information digitally. EHRs can include a wide range of data, such as medical histories, treatment plans, laboratory results, and imaging studies. Despite the shift towards digital storage, many healthcare providers still maintain physical records, especially in settings with limited resources or where digitization has not been fully implemented. Physical medical records are typically stored in secure filing systems within healthcare facilities. Individuals also have physical records stored electronically in various file formats (e.g., PDF), on personally held electronic media (e.g., CDs, USB drives, etc.), and physical paper records. In addition, individuals often monitor and collect health data themselves using smartwatches, fitness trackers, and at-home measurement devices. Such health data is typically accessed via a corresponding application (e.g., a smartphone application). Personal data can also be helpful and/or necessary in managing patient lives as well as health journeys. However, given the variety in data sources and formats, it can be difficult for individuals to monitor and control access to all of their data at any given time.

SUMMARY

At least one aspect of the present disclosure is directed to a method for providing a virtual health platform. The method includes receiving health data associated with a first user, assigning at least one data category to the health data, storing the health data in a database, receiving, from a second user, a request to access the health data, identifying a permission tier associated with the at least one data category assigned to the health data, and determining whether the second user has permission to access the health data based on the identified permission tier and an identity of the second user.

In some embodiments, the method includes analyzing the health data to identify the at least one data category. In some embodiments, the at least one data category corresponds to at least one of a data type, a data format, a data source, and a data timeframe. In some embodiments, receiving the health data associated with the first user includes receiving the health data from the first user. In some embodiments, receiving the health data associated with the first user includes receiving the health data from one of a medical provider, a pharmacy, a medical insurance provider, or an electronic data provider.

In some embodiments, the method includes receiving, from the first user, an assignment of the permission tier to the at least one data category. In some embodiments, the method includes receiving, from the first user, a selection of one or more permission tiers that the second user is permitted to access. In some embodiments, the method includes determining one or more permission tiers that the second user is permitted to access based on the identity of the second user. In some embodiments, receiving the request from the second user to access the health data includes receiving an indication of an event associated with the first user. In some embodiments, the method includes determining one or more permission tiers that the second user is permitted to access based on the identity of the second user and the event associated with the first user. In some embodiments, the method includes authenticating the identity of the second user.

Another aspect of the present disclosure is directed to a system for providing a virtual health platform. The system includes at least one memory for storing computer-executable instructions and at least one processor for executing the instructions stored on the at least one memory. Execution of the instructions programs the at least one processor to perform operations that include receiving health data associated with a first user, assigning at least one data category to the health data, storing the health data in a database, receiving, from a second user, a request to access the health data, identifying a permission tier associated with the at least one data category assigned to the health data, and determining whether the second user has permission to access the health data based on the identified permission tier and an identity of the second user.

In some embodiments, execution of the instructions programs the at least one processor to perform operations that include analyzing the health data to identify the at least one data category. In some embodiments, the at least one data category corresponds to at least one of a data type, a data format, a data source, and a data timeframe. In some embodiments, receiving the health data associated with the first user includes receiving the health data from the first user. In some embodiments, receiving the health data associated with the first user includes receiving the health data from one of a medical provider, a pharmacy, a medical insurance provider, or an electronic data provider.

In some embodiments, execution of the instructions programs the at least one processor to perform operations that include receiving, from the first user, an assignment of the permission tier to the at least one data category. In some embodiments, execution of the instructions programs the at least one processor to perform operations that include receiving, from the first user, a selection of one or more permission tiers that the second user is permitted to access. In some embodiments, execution of the instructions programs the at least one processor to perform operations that include determining one or more permission tiers that the second user is permitted to access based on the identity of the second user. In some embodiments, receiving the request from the second user to access the health data includes receiving an indication of an event associated with the first user. In some embodiments, execution of the instructions programs the at least one processor to perform operations that include determining one or more permission tiers that the second user is permitted to access based on the identity of the second user and the event associated with the first user. In some embodiments, execution of the instructions programs the at least one processor to perform operations that include authenticating the identity of the second user.

DETAILED DESCRIPTION

Figure 1:
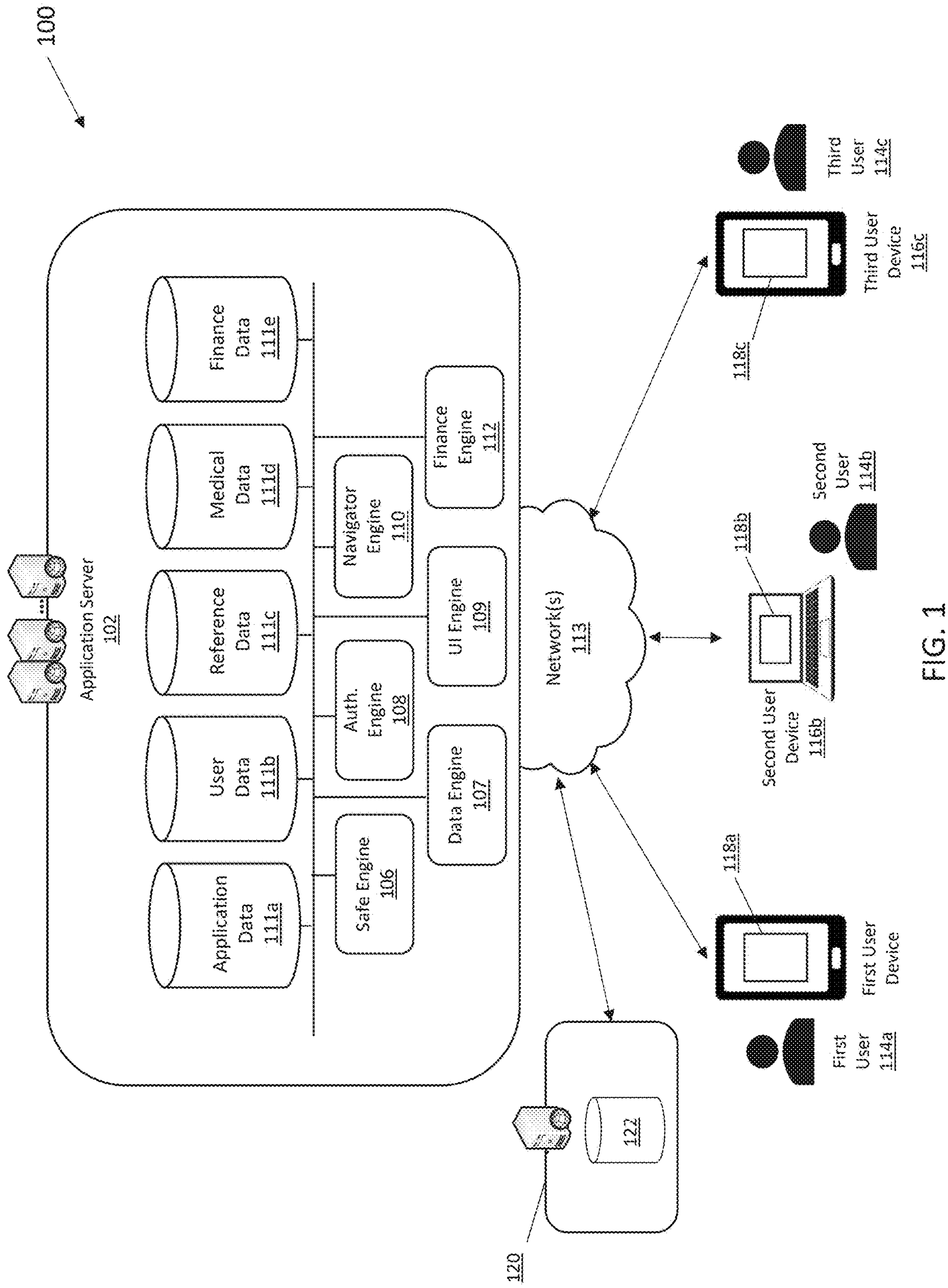
FIG. 1 is a block diagram of a virtual health platform in accordance with aspects described herein.

As described above, health or medical data is typically stored using a combination of electronic and physical records. Such data can include sensitive and/or non-sensitive information. For example, health data may include information such as: patient demographics (e.g., basic information such as name, date of birth, gender, address, and contact details), identification numbers (e.g. medical record numbers), medical histories (e.g., detailed records of past medical conditions, surgeries, hospitalizations, allergies, and family health history), medications (e.g., information on current and past medications, including dosages, frequency, and prescribing physicians), immunization records (e.g., documentation of vaccinations received and due dates for upcoming immunizations), lab results (e.g., results from blood tests, urine tests, EKGs/ECGs, and other laboratory work, including any notes or interpretations by medical professionals), radiology images and reports (e.g., digital images from X-rays, MRIs, CT scans, and ultrasounds, along with associated reports), progress notes (e.g., ongoing notes from healthcare providers documenting patient visits, treatment plans, and clinical observations), vital signs (e.g., records of vital statistics such as blood pressure, heart rate, temperature, and respiratory rate over time), medical device data (e.g., implantable cardioverter defibrillator, continuous glucose monitor, neural implant, etc.), wearable device (e.g., fitness trackers and smart watches) and/or self-monitored data (e.g., sleep data, heart rhythm, neuro monitoring, blood glucose, period tracking for women, headache patterns, etc.), data and/or information summaries (e.g. provider lists, preferred medical facilities, critical information in case of an emergency, AI/ML or other algorithmically generated or derivative data sets or summaries), emergency contact lists, legal documents and/or directives, health insurance and billing information (e.g., details of medical billing and insurance claims, including codes for diagnoses and procedures), and any AI/ML or other algorithmically generated or derivative data..

It should be appreciated that the sensitivity levels of health data vary on a patient-by-patient basis. For example, one patient may be comfortable sharing a portion of their health data with a medical practitioner or family member, whereas another patient may be uncomfortable sharing the same data. Often times, patients are unable to control (or restrict) access to their health and/or personal data in a manner that suits their privacy preferences. Further, the ability to access and/or distribute health (or personal) data may be restricted based on where or by whom the data is stored (e.g., at a medical provider's facility, in remote servers storing provider data, at a law firm, etc.). As a result, it has become increasingly difficult for patients to locate, monitor, and/or distribute their own medical records given the number of data handlers and storage locations. Accordingly, a personal data safe is needed for virtual health and other personal uses that enables control and use of personal and health data when and where an individual chooses and provides each individual user with his or her own data that can be used in conjunction with AI, ML and algorithmic models and applications.

Systems and methods directed to an integrated virtual health platform and personal data safe are provided herein. In some embodiments, the virtual health platform is configured to provision medical or health data, regulate access to medical or health data, and authenticate users associated with medical or health data.

FIG. 1 is a block diagram of an integrated virtual health platform 100 in accordance with aspects described herein. In one example, the platform 100 is implemented by an application server 102. The application server 102 provides functionality for provisioning health data, regulating user access to health data, and authenticating users. The application server 102 comprises software components and databases that can be deployed at one or more data centers (not shown) in one or more geographic locations, for example. The application server 102 software components may include a safe engine 106, a data engine 107, an authentication engine 108, a user interface (UI) engine 109, a navigator engine 110, and a finance engine 112. In some examples, the finance engine 112 corresponds to (or includes) an insurance engine. The software components can comprise subcomponents that can execute on the same or on a different individual data processing apparatus. The application server 102 databases include an application data database 111*a*, a user data database 111*b*, a reference data database 111*c*, a medical data database 111*d*, and a finance data database 111*e*. In some examples, the finance data database 111*e* corresponds to (or includes) an insurance database. The databases can reside in one or more physical storage systems. Example features of the software components and data processing apparatus will be further described below. It should be appreciated that the application server 102 may include or otherwise support additional engines and tools. For example, the application server 102 may support third-party tools that provide additional functions to the engines 106-112 and/or the databases 111*a*-111*e*. In some examples, the application server 102 is configured to utilize one or more Application Programming Interfaces (APIs) to communicate with third-party tools and engines. In some examples, the application server 102 is configured to communicate with artificial intelligence (AI), machine leaning (ML), or other algorithmic models or platforms. Such AI, ML, or other algorithmic models/platforms may be located in the cloud (e.g. hosted by a third party server), locally (e.g., hosted by the application server 102), and/or on a client device (e.g., user device 116).

The application server 102 is configured to send and receive data to and from users'client devices (e.g., user device 116) through one or more data communication networks 113 such as the Internet, for example. The user can access a user interface of a client application 118. In some examples, the client application 118 is configured to run in a web browser or a special-purpose software application executing on the user device 116. Although this application will describe many functions as being performed by application server 102, in various implementations, some or all functions performed by application server 102 may be performed locally by a client application (e.g., client application 118). The client application 118 can communicate with the application server 102 over the network(s) 113 using Hypertext Transfer Protocol (HTTP), another standard protocol, or a proprietary protocol, for example. The user device 116 can be a mobile phone, a smart watch, a laptop, a tablet computer, a personal computer, a game console, a virtual reality (VR) headset or console, an augmented reality (AR) device, a pair of VR/AR glasses, an ambient listening, speech or other recording or communication device, a set-top box, a data device, or a connected media device. In some examples, the user device 116 is a wearable smart device, a non-wearable smart device, or a smart device embedded within another item or device. Other types of user devices are possible. In some examples, the user device 116 is configured to communicate with various sensors and devices, such as, for example, in-ear audio devices and ambient audio devices (e.g., microphones, speakers, etc.).

Figure 2:
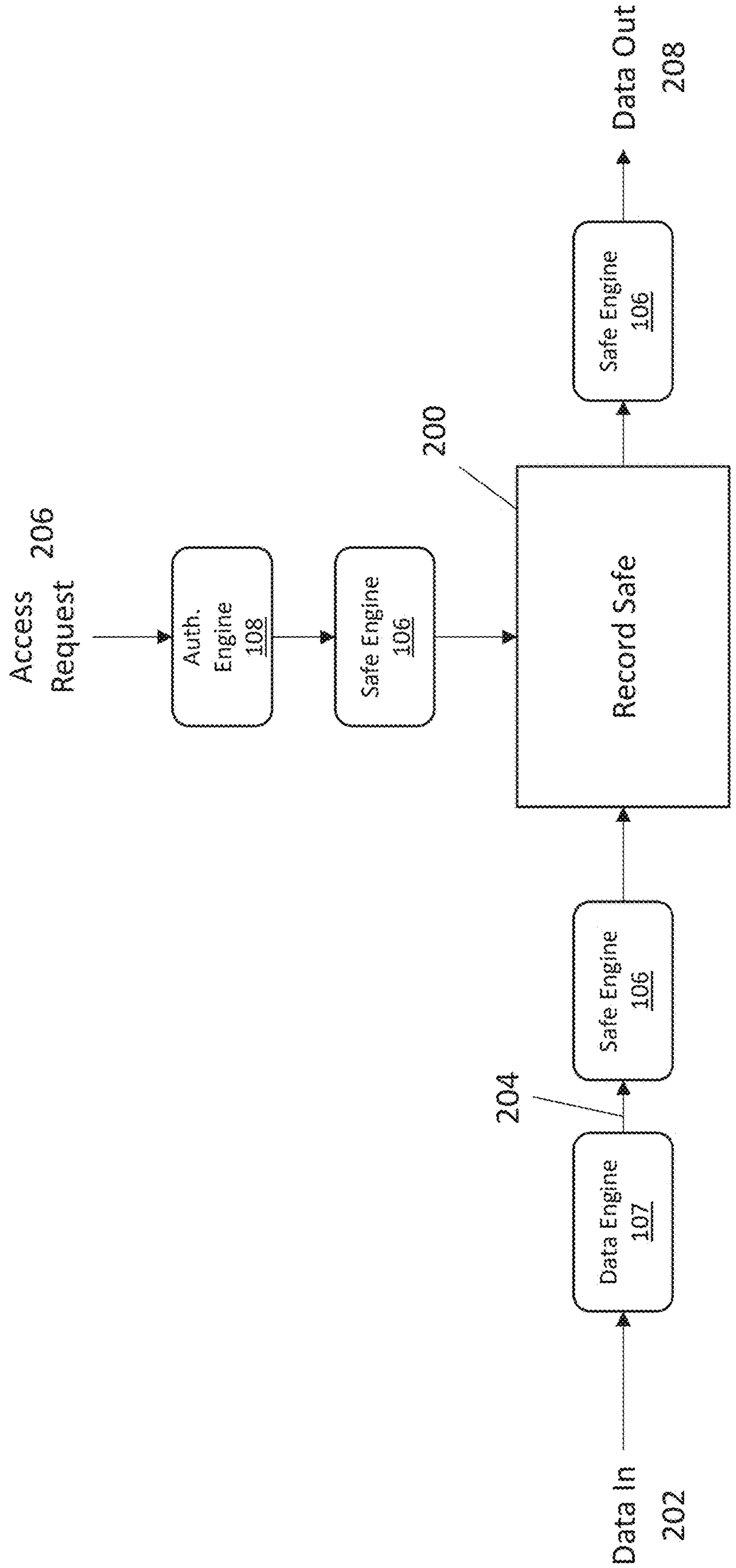
FIG. 2 is a flow diagram illustrating operation of a record safe in accordance with aspects described herein.

In various implementations, the platform 100 can provide a record safe (or vault) for storing personal medical records and health data (e.g., of the first user 114*a*). In some examples, the platform 100 is configured to provide security for the record safe as well as security for the individual medical records (or health datasets). FIG. 2 is a flow diagram illustrating operation of the record safe 200. In some examples, the record safe 200 (or the platform 100) receives input health data 202 from an individual or patient (e.g., the first user 114*a*), a medical practitioner (e.g., the second user 114*b*), or a family member, guardian, or friend (e.g., the third user 114*c*). In some examples, the record safe 200 receives input health data 202 from a third-party database (e.g., database 122 of server 120 in FIG. 1). The database 122 may be associated with a medical provider (e.g., a hospital, doctor's office, medical lab, etc.), a medical platform (e.g., electronic health or medical record application, patient portal, consumer health or data application, etc.), an insurance company, a pharmacy, a pharmacy benefit provider, a government entity, a healthcare entity, a health advocacy entity, a health management entity, a finance entity, or other entities that may store or transmit relevant data. In some examples, the database 122 corresponds to data from a health or fitness application associated with a wearable device or another type of connected device. The input data 202 may be electronic medical records, PDFs, copies of paper records, photos, raw datasets, graphs, metrics, reports, or any other suitable type of health, medical, and/or personal data.

In some examples, the input health data 202 is provisioned by the platform 100. For example, the data engine 107 may be configured to provision the input health data 202. In some examples, the data engine 107 periodically queries available data sources that are known to be associated with the first user 114*a*. For example, the first user 114*a* may link their preferred (or assigned) medical practitioners or providers via the client application 118*a* such that the data engine 107 can identify the appropriate data sources (or entities housing data sources) to query. Likewise, the user 114*a* may link third party applications, wearable devices, implanted devices, and other smart or linkable devices (or the associated applications) for data queries. In some examples, the data engine 107 uses one or more APIs to interface with the various data sources. The data engine 107 may query such data sources hourly, daily, weekly, monthly, or over any other desired interval. In some examples, the user 114*a* can adjust the interval based on their personal preferences (e.g., via the client application 118*a*). In some examples, the platform 100 may detect the frequency of medical activity or procedures associated with the user 114*a* and automatically adjust the interval accordingly. It should be appreciated that such requests or queries may be automatically sent by the platform 100 via APIs, email, fax, phone, or other suitable techniques.

In some examples, the user 114*a* assists with the data provisioning process. For example, the user 114*a* may email, fax, upload, and/or scan copies of medical forms, records, files, and data to be added to the record safe 200. In such examples, the data engine 107 is configured to receive the input health data 202 directly from the user. In some examples, the user 114*a* sends the input health data 202 to a temporary location (e.g., a digital mailbox, a database, etc.) where it is retrieved by the data engine 107. The data engine 107 may be configured to check the temporary location periodically or it may receive a notification to check the temporary location for data retrieval. It should be appreciated that medical practitioners, medical providers, insurance companies, family members, and the like may submit medical records and health data for entry into the record safe 200 using similar techniques.

While the above examples refer to the input data 202 as medical and health data, it should be appreciated that the input data received for an individual may include other types of personal data. For example, the input data 202 may include bank account information, power of attorney information, legal documents and/or directives, demographic information, and legal data (or records). The input data 202 may include, for example, the individual's full legal name, maiden name, aliases, home address, previous addresses, phone numbers, email addresses, date of birth, place of birth, Social Security number, driver's license number, passport number, state ID number, employee ID number, student ID number, bank account number, credit or debit card number, tax identification number, medical record number, health insurance policy number, prescription and/or non-prescription pharmaceutical history, vitamin, nutritional, herbal and/or wellness supplement history, genetic information and/or test results, biometric fingerprints, facial recognition data, iris scans, voiceprints, retina scans, dental and/or orthodontic records, personal and/or patient notes, transcripts or diaries, appointment records and/or calendar information, therapy session notes, disability status, blood type, allergy information, emergency contact details, marital status, names of family members, dependent information, children's names, children's birthdates and/or birth records, adoption records, foster care records, marriage records, divorce records, guardianship and/or custodial documents, documents relating to care of parents and/or other adult or minor-aged family members, documents relating to the work-related, volunteer or other care of unrelated children and/or adults, employment history, salary and/or other compensation-related information, pension details, union membership, work performance reviews, disciplinary records, education history, transcripts, school enrollment records, standardized test scores, religious affiliation, political affiliation, voting history, membership in clubs, advocacy groups or associations, travel documents and/or history, visa information, immigration records, citizenship status, criminal records, arrest history, court records, incarceration history, parole information, military service records, veteran status, IP address, MAC address, device serial numbers, GPS location data, Wi-Fi connection history, browsing history, search engine queries, social media profiles, usernames, passwords, security questions and/or their answers, private messages, online purchase history, shopping preferences, loyalty card numbers, subscription records, photographs, video recordings, audio recordings, personal preferences, device settings and/or preferences, vehicle registration numbers, license plate numbers, VIN numbers, property ownership records, and/or AI, ML and/or other algorithmic model or platform generated personal data, relationships, preferences, settings, etc. that may be relevant to the user.

In some examples, the data engine 107 is configured to convert the input health data 202 into one or more standardized formats (i.e., converted health data 204). For example, the data engine 107 may convert all input health data 202 into a PDF format, a JPEG format, a database format, or any other preferred format. In some examples, the standardized format selected for a particular data item (or record) depends on the type of data or record. For example, all images from radiology may be converted into a first format (e.g., JPEG), all medical records may be converted into a second format (e.g., PDF), all wearable data may be converted into a third format (e.g., a predetermined data table), and so on. Likewise, a range of standardized formats may be used for particular types of records. For example, a range of standardized formats may be assigned to radiology images. In such examples, a first format may be selected for x-rays, a second format may be selected for MRIs, and so on. In some examples, the data engine 107 is configured to perform one or more pre-processing functions on the converted data. For example, the data engine 107 may process PDF files to enable optical character recognition (OCR) capabilities, such that that the PDF files may be searched easily. Likewise, the data engine 107 may process (or condition) image files for compatibility with computer vision and image processing functions. In some examples, the data engine 107 is configured to perform steps to normalize and clean text, such as tokenizing content, removing punctuation, and filtering out duplicate content.

The safe engine 106 is configured to assign data categories to the converted input health data 204. In some examples, the safe engine 106 includes one or more artificial intelligence (AI) models or machine learning (ML) models that are trained to identify data categories corresponding to the data 204. In some examples, the safe engine 106 includes a neural network and/or large language model (LLM) that is trained to search the converted health data 204 to locate and identify data categories associated with the data. In some examples, computer vision and image processing functions are used to search the converted health data 204 to locate and identify data categories associated with the data. The safe engine 106 may look for keywords, terms, phrases, codes (e.g., insurance codes or medical codes), medicines, machines, materials, or any other type of indicator that may be useful in identifying data categories. In some examples, the safe engine 106 infers one or more data categories associated with the converted health data 204 based on the source of the data (e.g., the medical provider that uploaded the data, the location of the server or database that provided the data, etc.). In some examples, the safe engine 106 is configured to perform the category assignments using one or more algorithms. For example, the algorithms may be configured to assign categories to the converted health data 204 based predetermined or dynamic relationships (e.g., based on the preferences of the user or industry/social trends). It should be appreciated that the safe engine 106 may be configured to assign data categories to the input health data 202, rather than the converted health data 204.

The data categories may include, for example, data type, medical condition, medical diagnosis, medical provider, medical institution, date or timeframe, source device, wearable type, location, or any other suitable data category. In some examples, the safe engine 106 assigns the identified data categories to the entire health record (or dataset). In some examples, the safe engine 106 assigns identified data categories to portions or sections of the health record (or dataset). For example, the entire medical record may be assigned a first data category (e.g., PDF), a first section of the medical record may be assigned a second data category (e.g., Condition A), a second section of the medical record may be assigned a third data category (e.g., Condition B), a third section of the medical record may be assigned a fourth category (e.g., Data Type A), and so on.

In some examples, the safe engine 106 is configured to prompt the user 114*a* to identify data categories associated with the converted health data 204. The safe engine 106 may provide one or more instructions to the UI engine 109 to generate user prompts that are presented via the client application 118*a*. In some examples, the user 114*a* is presented with an entire medical record (or dataset) and asked to assign the relevant data categories. In other examples, the user 114*a* is presented with one or more sections (or portions) of a medical record or dataset for category assignment. In some examples, the safe engine 106 provides one or more predicted data categories that the user 114*a* selects from during the data category assignment process. In some examples, the safe engine 106 predicts and assigns one or more data categories that the user 114*a* may edit. Such predicted data categories may be generated using one or more AI/ML models of the safe engine 106, as discussed above.

Once the data categories have been assigned, the converted health data 204 is stored or saved in the record safe 200. In some examples, the record safe 200 corresponds to a database or a portion of a database (e.g., medical data database 111*d*). In some examples, each user 114 has their own instance of the record safe 200. In other words, each record safe 200 may be configured to store health data associated with a corresponding user 114. In some examples, each user 114 shares the record safe 200 with a population of users. For example, each user 114 may have a dedicated portion (or partition) of the record safe 200 that is separate from the user portions. In some examples, the assigned data categories may be stored in the record safe 200 with the converted health data 204. In some examples, the assigned data categories are stored in a separate database (e.g., application data database 111*a* or reference data database 111*c*). In such examples, the safe engine 106 may use a lookup table or another reference to map the assigned data categories to the converted health data 204 stored in the record safe 200. In some examples, an algorithm or AI/ML technique is used to map the assigned data categories to the converted health data 204 stored in the record safe 200.

While the above embodiments describe converting the input health data 202 before storing the data in the record safe 200, it should be appreciated that the input health data 202 may be stored in the record safe 200 before it is converted or cleaned to provide the converted health data 204. Likewise, while the above embodiments describe assigning data categories to the converted health data 204 before the data is stored in the record safe 200, it should be appreciated that the input health data 202 and/or the converted health data 204 may be stored in the record safe 200 before the data categories are identified/assigned.

The platform 100 provides separate secure authorization credentials for each person, entity, or person within an entity authorized to obtain contents from the record safe 200. In some examples, the contents of the record safe 200 that are permissioned to each authorized user is different (i.e., not everyone is permissioned to see the full contents of the record safe 200 they are authorized to enter). Each user 114 can only access what they are permissioned to access, based on their individual authorization credentials to the record safe 200. In other words, each user 114 has access to an individualized-safe within the record safe 200, where the content of the individualized-safe corresponds to the user's permissions. For example, the first-party user 114*a* (e.g., the subject of the health data) may be assigned an authorization credential that grants them full access to their own record safe 200 (or dedicated portion of a common record safe). As such, the first-party user's 114*a* individualized-safe corresponds to the entire record safe 200. The first party-user 114*a* may grant access to third-party users (e.g., users 114*b*, 114*c*) that spans from no access up to full access, as indicated by corresponding authorization credentials. As such, the accessible content of each third-party user's 114 individualized-safe may vary based on the permissions assigned to the user. In some examples, the authorization credentials assigned to each user are stored in the user data database 111*b*. In some examples, a third-party user is permitted to have a higher level of access than the first-party user. For example, a guardian (e.g., a parent) may be a third-party user that has a higher level of access than the first-party user (e.g., their child). Likewise, a health care agent or proxy may be a third-party user that has at least the same level of access as the first-party user (e.g., their parent).

In some examples, each third-party user is assigned access based on a plurality of tiers. In one example, each tier corresponds to a level of privacy or sensitivity. For example, in a three-tier system, Tier 1 may represent access to a content range requiring a high level of privacy, corresponding to the most private or sensitive data. Likewise, Tier 2 may represent access to a content range requiring a medium level of privacy and Tier 3 may represent access to a content range requiring a low level of privacy (or a non-private level). It should be appreciated that the number of tiers for the record safe 200 may be configured by the first-party user 114*a*. For example, the user may elect to use three tiers, four tiers, ten tiers, and so on. In some examples, the user may elect to use two tiers (e.g., private and non-private).

Figure 3:
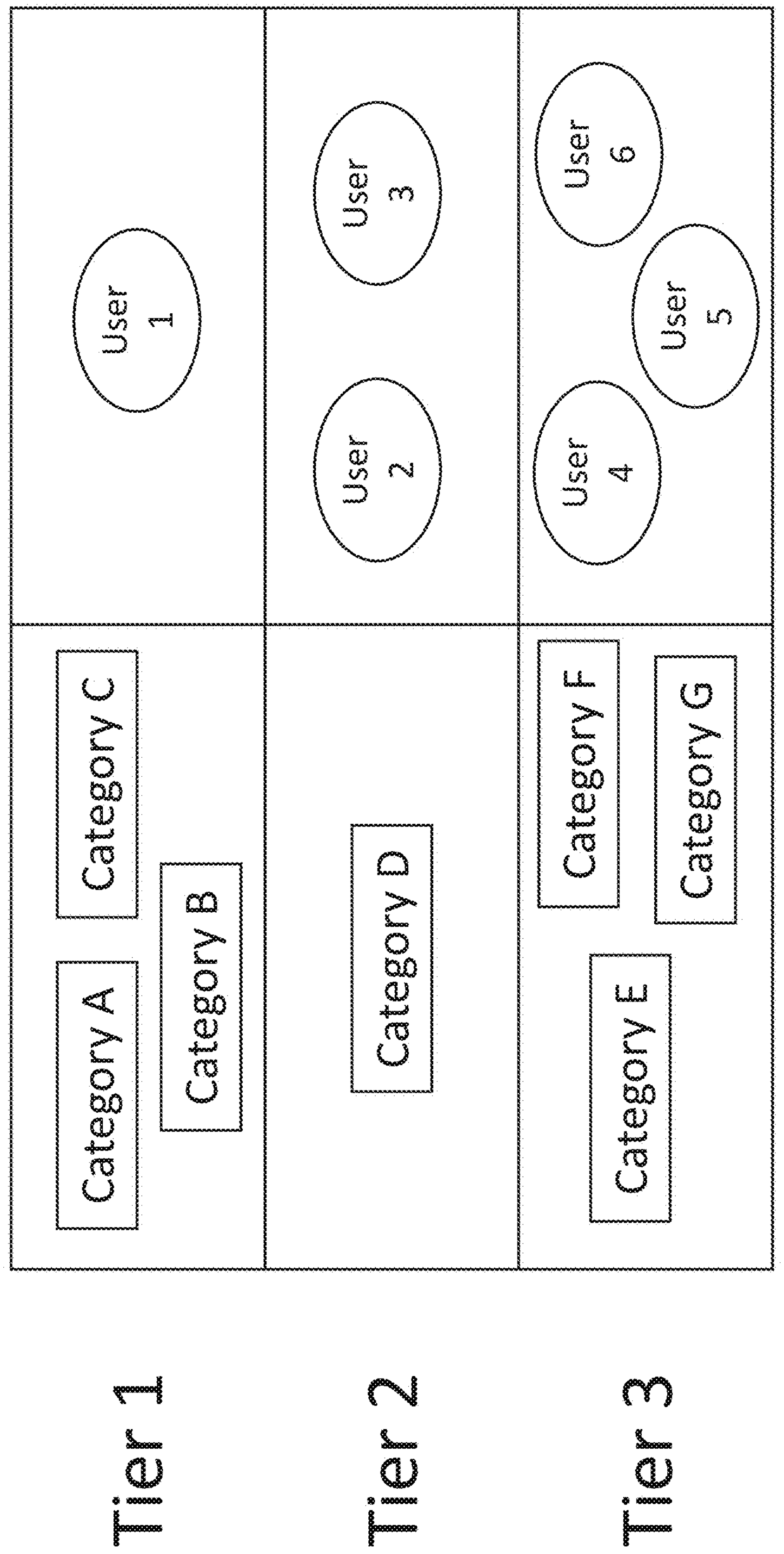
FIG. 3 is a diagram illustrating example assignments of data categories and users to permission tiers in accordance with aspects described herein.

In some examples, one or more data categories are assigned to each tier based on the user's privacy preferences. FIG. 3 illustrates an example of category-to-tier assignments. As shown, Category A (e.g., Medical Institution A), Category B (e.g., blood test data), and Category C (e.g., x-ray images) are assigned to Tier 1, Category D (e.g., Medical Provider A) is assigned to Tier 2, and Category E (e.g., Medical Institution B), Category F (e.g., Medical Provider B), and Category G (e.g., heart rate data) are assigned to Tier 3. In the event of a tier conflict (e.g., x-ray images (Tier 1/Category C) from Medical Institution B (Tier 2/Category E)), the tier assignment may be handled in accordance with the user's preferences. In some examples, the user is alerted of the tier conflict (e.g., via the client application 118) and prompted to select a tier for assignment (e.g., Tier 1 or Tier 2). In some examples, the corresponding data is automatically assigned to a tier based on a predetermined user setting (e.g., elevate the data to the highest relevant tier (e.g., Tier 1)). In some examples, the category-to-tier assignments are performed using one or more algorithms. For example, the algorithms may be configured to assign categories to tiers based predetermined or dynamic relationships (e.g., based on the preferences of the user or industry/social trends). In some examples, the assignments are reviewed by the first-party user 114*a*.

In some examples, each category-to-tier assignment is made by the first-party user 114*a*. The safe engine 106 may provide one or more instructions to the UI engine 109 to generate user prompts that are presented via the client application 118*a*. In some examples, the user 114*a* assigns each data category to a tier (e.g., Tiers 1-3) via the client application 118*a*. In some examples, the user 114*a* is prompted to make data category assignments upon creating a user account on the client application 118*a* and establishing the record safe 200. In some examples, the user-specific data category assignments are stored in a database (e.g., user data database 111*b*). In some examples, the user 114*a* is prompted to assign new data categories to tiers as they are discovered or detected by the safe engine 106 from the converted health data 204.

In some examples, the category-to-tier assignments are performed using generalized category groups. For example, the user may assign all "Lab Results" to Tier 1, where all data categories falling under "Lab Results" are assigned to Tier 1, and so on. Likewise, all data and records relating to a specific health condition may be assigned to the same tier. For example, all data and records relating to diabetes may be assigned to Tier 1, all data and records relating to infertility may be assigned to Tier 2, and so on. In some examples, the category-to-tier assignments are performed using generalized profiles. For example, the user may select a privacy profile (e.g., Very Private, Sometimes Private, Not Private, etc.) that corresponds to a predetermined mapping of data categories to tiers. Likewise, the user may select a privacy level (e.g., 1 to 10) that corresponds to a predetermined mapping of data categories to tiers.

While the above embodiments describe assigning categories to tiers, it should be appreciated that the safe engine 106 may assign tiers directly to the data (e.g., the input health data 202 or the converted health data 204). For example, the safe engine 106 may assign a data item (e.g., file, photo, etc.) or a portion of a data item to a tier (e.g., Tier 1, 2, or 3). In some examples, the safe engine 106 is configured to perform the data-to-tier assignments using one or more algorithms. For example, the algorithms may be configured to assign tiers to the health data 202/204 based predetermined or dynamic relationships (e.g., based on the preferences of the user or industry/social trends).

It should be appreciated that other types and configurations of tier assignments may be contemplated. In some examples, one or more data categories may be included in multiple tiers. For example, data category A may be assigned to Tiers 1 and 2. Likewise, global tiers may be used that grant access to all data categories. In some examples, the tiers are used as groups of data categories, rather than a hierarchy of tiers. In such examples, users assigned to one tier/group (e.g., Tier 1) may not have access to some or all of the data categories assigned to other tiers/groups (e.g., Tiers 2 and 3).

As described above, the first-party user 114*a* may grant access to third-party users (e.g., users 114*b*, 114*c*) that spans from no access up to full access. To provide such access, the first-party user 114*a* assigns tiers to each third-party user. For example, as shown in FIG. 3, User 1 has been assigned Tier 1 access, which grants them access to Tiers 1-3 (i.e., Data Categories A-G). Users 2 and 3 have been assigned Tier 2 access, which grants them access to Tiers 2 and 3 (i.e., Data Categories D-G). Users 4, 5, and 6 have been assigned Tier 1 access, which grants them access to Tier 1 only (i.e., Data Categories E-G). In some examples, the user 114*a* assigns individual tiers to users. For example, the user 114*a* may assign access to Tiers 1 and 3 to a user, restricting the user from accessing Tier 2.

Figure 4:
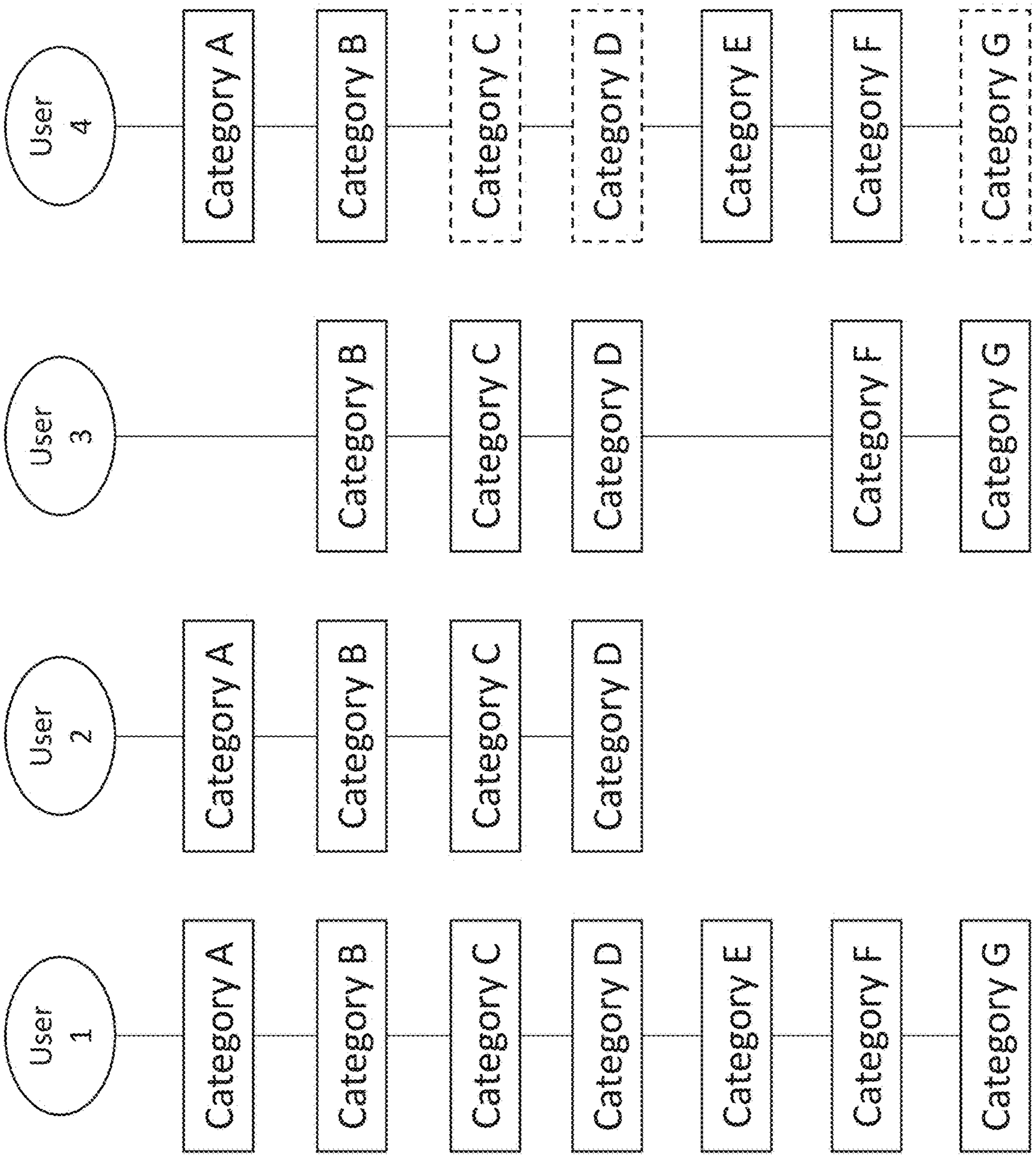
FIG. 4 is a diagram illustrating example assignments of data categories to users in accordance with aspects described herein.

In some examples, the first-party user 114*a* assigns data categories directly to users for access (e.g., via the client application 118*a*). FIG. 4 illustrates an example of category-to-user assignments. As shown, User 1 has been granted access to Data Categories A-G, User 2 has been granted access to Data Categories A-D, and User 3 has been granted access to Data Categories B-D, F, and G. The user 114*a* may assign data categories to particular users for access on a conditional basis. As shown in FIG. 4, User 4 has been assigned regular access to Data Categories A, B, E, and F and conditional access to Data Categories C, D, and G. The conditional access is granted based on or more conditions established by the first party user 114*a*. For example, conditional access may be granted based on a life threating medical condition, the first-party user 114*a* reaching a certain age, the third-party user (e.g., user 114*b* or 114*c*) reaching a certain age, or any other conditions that may be desired by the first-party user 114*a*. It should be appreciated that the tier-level access as shown in FIG. 3 may also be granted on a conditional basis. In addition, it should be appreciated that the users in the examples described above may be specific individuals or classes of individuals. For example, each user may correspond to a person (e.g., John Smith, my son, my doctor, etc.) or a class (e.g., emergency medical personnel, nurses, doctors, employees of Medical Institution A, etc.). In other words, the users that are assigned to tiers and/or data categories may be individuals, classes of individuals, individuals having specific job titles, individuals working at specific facilities, organizations, etc. It should be appreciated that conditional access includes temporal access, where a user is granted specific access for a defined period of time.

In some examples, an activity sequence is used to determine which permission tiers (e.g., Tiers 1-3) are associated with particular activities (or events). For example, routine activities (e.g., regular appointments, prescription orders, etc.) may be associated with lower permission tiers (e.g., Tiers 1 and 2). As such, specific third-party users (e.g., family members, service providers, pharmacists, etc.) that have lower-level permission access may be notified or called in response to the occurrence of relevant activities assigned to such tiers. Likewise, these third-party users may be notified or called when the primary user 114*a* requests an activity/event (e.g., orders new medication, schedules an appointment, etc.). On the other hand, emergencies or urgent events (e.g., injuries, hospital visits, irregular biometrics, etc.) may be associated with higher tiers (e.g., Tier 3). Certain third-party users (e.g., close family members, doctors, emergency personnel, etc.) that have higher-tier permission access may be notified or called in response to the occurrence of each relevant activity assigned to the higher tier. In some examples, third-party users with higher-level permissions (e.g., Tier 3) may receive notice of all activities or relevant activities associated with lower-level permissions (e.g., Tiers 1 and 2). In some examples, a notification may be sent to all third-party users in response to an emergency event. In some examples, the activity sequence includes an order of third-party users that are notified based on the occurrence of an event (e.g., an emergency). In such examples, each third-party user may be notified in a sequence. Alternatively, a third-party user may only be notified in the event the immediately preceding third-party user could not be reached.

It should be appreciated that the tiers/groups used in connection with activity sequences may be the same or different from those used for data permissions. In other words, all users with Tier 1 permissions for data access may not have the same activity sequence status. In some examples, the type of notice provided to a user depends on the tier/group assigned with respect to the activity sequence. For example, higher level users may receive phone calls, whereas lower level users may receive text messages or push notifications. Other types of notification configurations and methods may be contemplated. In some examples, the type of notice, or decision to provide notice, is conditioned on (i) the type of activity/event and (ii) the time or place of the activity/event. For example, if a child is injured on a weekday during the school year, the activity sequence may prioritize notice to the school nurse (or other officials). On the other hand, if a child is injured on the weekend, the activity sequence may prioritize notifying the parents, and may not notify the school nurse (or official) at all.

In some examples, the first party user 114*a* determines which activities or events are assigned to individual permission tiers. For example, the user 114*a* may assign generalized categories (e.g., "Emergencies") and/or specific events (e.g., "Car crash") to one or more permission tiers. In some examples, a representative (e.g., third-party user) of the user 114*a* determines how specific activities or events are assigned to the permission tiers. For example, a doctor of the user 114*a* may assign a particular medication prescription to one or more permission tiers (or individual third-party users within the tiers). In such examples, the third-party users associated with the assigned tiers may be notified if the user 114*a* fails to take the medication, order the medication, pick up the medication, etc. In some examples, an algorithm or AI/ML technique is used to map activities or events to the various permission tiers (or third-party users).

Returning to FIG. 2, a user 114 can submit an access request 206 to the record safe 200 to access stored health data. The access request 206 may be submitted by the first party user 114*a* or third-party users (e.g., users 114*b*, 114*c*). The first-party user 114*a* may submit an access request 206 to view their own data or to send data to a third-party user 114. When submitted by a third-party user 114, the access request 206 may include the identity of the requesting user 114 (i.e., the third-party user) and the identity of the user whose data is being accessed (i.e., the first-party user). In some examples, the access request 206 is a general request to access the record safe 200. In other examples, the access request 206 includes an indication of specific data being requested (e.g., blood test results from July 2016, physical report from Medical Institution A, etc.).

The access request 206 is generated using the client application 118. For example, the first-party user 118*a* may utilize the client application 118*a* to submit an access request 206 corresponding to their own health data (i.e., own record safe 200). Likewise, third-party users may utilize the client application 118 to generate and submit the access request 206. The third-party users may be presented with a search window, dropdown menu, or another UI mechanism to select the first-party user 114*a* associated with the access request 206. In some examples, the identity of the first-party user is unknown to the third-party user submitting the access request 206 (e.g., in an emergency situation). In such examples, the third-party user may scan a QR code, an RFID tag, or other identifying mechanisms that provides data and/or the identity of the first-party user 114*a*. In some examples, the third-party user submits an image of the first-party user 114*a* or an identification item (e.g., an ID, license plate, etc.) that is processed by the platform 100 to identify the first-party user 114*a*.

The access request 206 is initially received by the authentication engine 108. The authentication engine 108 is configured to determine and verify the identity of the user 114 submitting the access request 206. In some examples, access request submissions are available to third-party users 114 that have created user accounts on the platform 100. The third-party user accounts may include identifying information such as, for example, the user's name, address, location, occupation, job title, employer, training background, education history, and other relevant information. The identifying information may be stored in the user data database 111*b*. When creating the user account, third-party users may be prompted to establish one or more authentication credentials that are used to login and access the account. In some examples, the authentication engine 108 is configured to process the one or more authorization credentials associated with the requesting user 114. The identity of the requesting user 114 may be verified using, for example: password-based authentication, two-factor authentication, multi-factor authentication, biometric authentication (e.g., fingerprint scanning, facial recognition, iris recognition, voice recognition, etc.), security tokens (e.g., hardware tokens or software/digital tokens), smart cards, public key infrastructure (PKI), CAPTCHA, risk-based authentication (e.g., level of authentication is adjusted based on factors such as location, device, and behavior), or other types of authentication techniques. It should appreciated that similar authentication techniques may be used to verify the identity of users when creating user accounts on the platform 100.

While not shown in FIG. 2, the authentication engine 108 may utilize similar techniques to determine and verify the identity of the first-party user 114*a* when providing the input health data 202. For example, the identity of the first-party user 114*a* may be confirmed before the input health data 202 is received or added to the record safe 200. Likewise, the identity of a third-party user (or facility) providing input health data 202 may be confirmed before the data is received or added to the record safe 200.

Once the identity of the requesting user 114 has been verified, the safe engine 106 is configured to determine whether the requesting user 114 has the proper data permissions for the request. In the event the requesting user 114 is the first-party user 114*a*, the first-party user 114*a* may be directed to the record safe 200 with full access. For third-party users 114, the safe engine 106 determines the tiers and/or data categories that the requesting user 114 has been granted permission to access (e.g., as shown in FIGS. 3, 4). In some examples, the safe engine 106 provides restricted access to the requesting user 114 based on the tiers and/or data that the requesting user 114 has access to. For example, User 2 of FIG. 3 may be able to access (or view) data in the record safe 200 that has been assigned to Tiers 2-3 (i.e., Data Categories D-G). As such, the Tier 1 data (i.e., Data Categories A-C) may be hidden, redacted, or otherwise unavailable to User 2. In some examples, when the access request 206 is submitted by the first-party user 114*a* to share (or send) data to a third-party user 114, the same permission restrictions apply. However, in such situations, the first-party user 114*a* may override the restrictions if desired (i.e., allowing the third-party user to view the restricted data).

As described above, the first-party user 114*a* may assign conditional access to tiers or data categories. In some examples, if the requesting user 114 does not have full access to the record safe 200, the safe engine 106 checks whether any conditional access conditions have been satisfied. In some examples, the access request 206 includes one or more conditions or events that have been submitted by the requesting user 114 (e.g., an emergency situation). In some examples, the safe engine 106 is configured to verify the accuracy of the reported conditions or events. For example, if a doctor at Hospital A submits a request under an emergency condition, the safe engine 106 may verify that the first-party user 114*a* has been admitted to Hospital A. Such verification may be performed using an API to access one or more databases of the Hospital A (e.g., database 122) or by contacting Hospital A (e.g., via automated email or AI-assisted telephone calls). In some examples, if the first-party user 114*a* is available, the safe engine 106 prompts the user 114*a* to approve the conditional access request. In some examples, one or more third-party users 114 are designated by the first-party user 114*a* to verify conditional access requests when the first-party user 114*a* is unavailable (e.g. unconscious). For example, User 2 in FIG. 3 may be designated by the first-party user 114*a* to verify conditional access requests for Tiers 2 and 3 in the event of an emergency. Likewise, User 1 in FIG. 3 may be designated by the first-party user 114*a* to verify conditional access requests for Tier 1 in the event of an emergency. In some examples, the requesting user 114 is asked to certify the accuracy of the reported conditions before conditional access is granted. In some examples, the requesting user 114 is asked to describe the present conditions (or injuries) and the safe engine 106 determines whether conditional access should be granted.

In some examples, the ability to export data from the record safe 200 depends on the preferences of the first-party user 114*a*. For example, the first-party 114*a* may disable the ability for data to be exported from the record safe 200 to ensure privacy is maintained. However, the first-party user 114*a* may enable data to be exported from the record safe 200 (i.e., as output health data 208). In such examples, the safe engine 106 is configured to prepare a redacted version of the health data based on the access request 206 and the permissions of the requesting user 114. In some examples, the safe engine 106 generates a report that includes only the requested data in view of the permissions of the requesting user 114. In some examples, the output health data 208 is delivered to a mailbox or another record safe within the client application 118 of the requesting user 114. In some examples, the output health data 208 expires at a predetermined time configured by the first-party user 114*a* (e.g., 1 day, 1 week, at the completion of treatment, etc.). In such examples, the output health data 208 is automatically removed from the client application 118 of the requesting user 114 upon expiration.

While not shown in FIG. 2, the authentication engine 108 may utilize techniques similar to those described above to determine and verify the identity of third-party users 114 when sharing output health data 208. For example, the identity of a third-party user 114 whom the first-party user 114*a* has selected to share data with may be confirmed before the output health data 208 is shared from the record safe 200.

Figure 5:
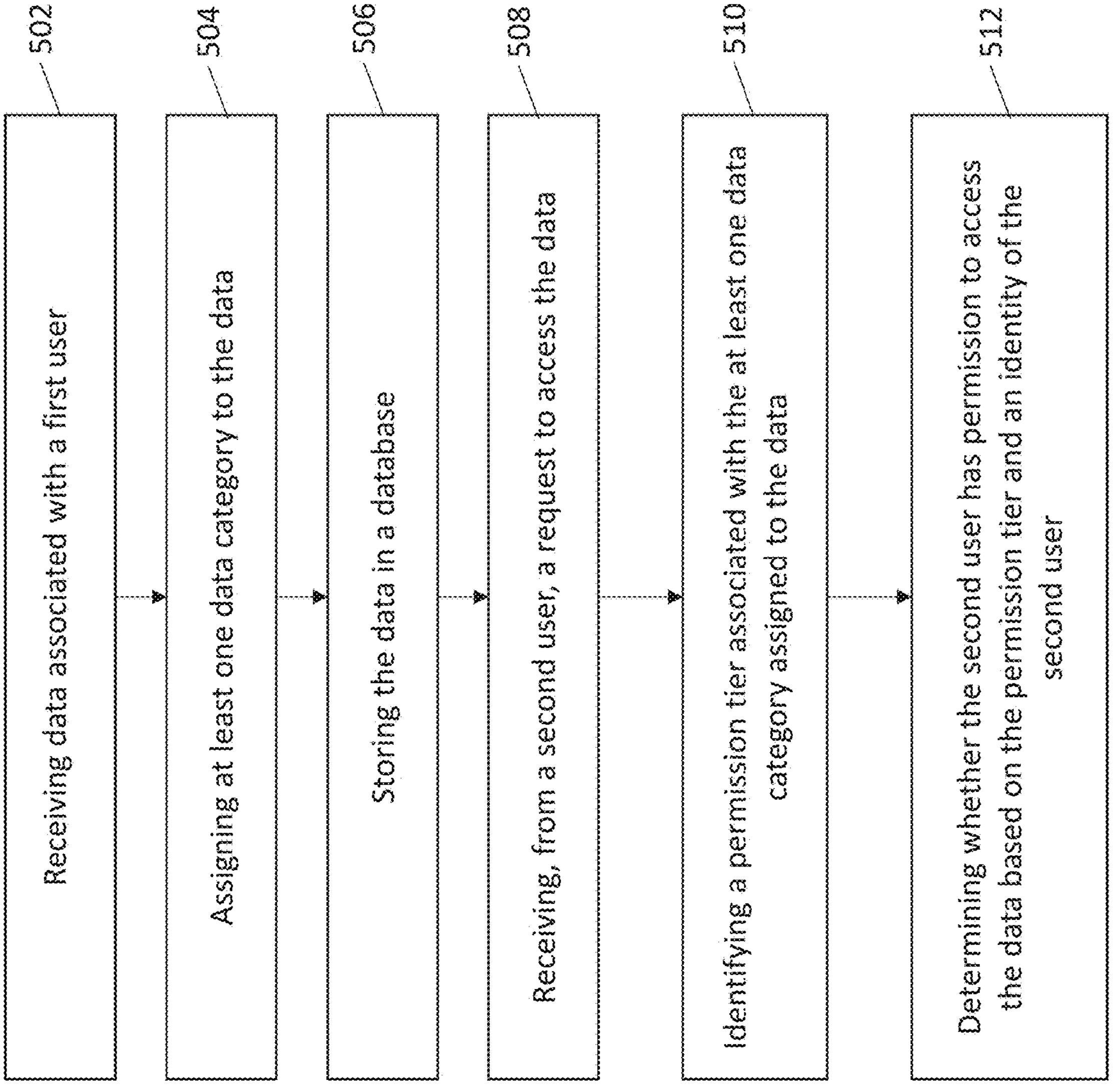
FIG. 5 is a flow diagram illustrating a method for providing a virtual data safe in accordance with aspects described herein.

FIG. 5 illustrates a flow diagram of a method 500 for providing a virtual data safe. In some examples, the method 500 corresponds the operation of the platform 100 for provisioning data, storing data in the record safe 200, and accessing data stored in the record safe 200. It should be appreciated that the data may be health data, medical data, personal data, or any other suitable type of data.

At step 502, the data engine 107 receives data (e.g., input health data 202) associated with a first user (e.g., the first-party user 114*a*). In some examples, the data engine 107 is configured to retrieve the input data 202. The data engine 107 may convert the input data into one or more standardized formats (e.g., converted health data 204).

At step 504, the safe engine 106 assigns at least one data category to the input data 202 (or the converted data 204). In some examples, the safe engine 106 is configured to assign data categories to the data using one or more AI/ML models. In some examples, the safe engine 106 (and the UI engine 109) provide prompts to the first-party user 114*a* to assign data categories to the data.

At step 506, the safe engine 106 stores the input data 202 (or the converted data 204) in the record safe 200. In some examples, the record safe 200 is a standalone database. In some examples, the record safe 200 is an isolated portion of a database (e.g., medical data database 111*d*).

At step 508, the authentication engine 108 receives a request to access data (e.g., the access request 206) from a second user (e.g., third-party users 114*b*, 114*c*). In some examples, the request 206 includes the identity of the second user or other identifying data. In some examples, the request 206 is a general request to access the record safe 200 (i.e., the second user's individualized version of the record safe 200). In some examples, the request 206 is a specific request regarding particular data stored in the record safe 200. In some examples, the authentication engine 108 is configured to verify the identity of the third-party user using one or more authentication credentials associated with the third-party user.

At step 510, the safe engine 106 identifies a permission tier associated with at least one data category assigned to the data stored in the record safe 200. In some examples, the safe engine 106 checks the permission tier(s) assigned to the data by the first-party user 114*a*. It should be appreciated that the order of steps 508 and 510 may be interchangeable. For example, the request 206 may be submitted after the safe engine 106 has identified the permission tier and/or data categories associated with the second user. In some examples, step 508 may be optional altogether (i.e., no request is submitted by the second user).

At step 512, the safe engine 106 determines whether the second user (i.e., the third-party requesting user) has permission to access the data based on the permission tier assigned to the data and the identity of the second user. In some examples, the first-party user 114*a* assigns one or more tiers to an individual user or a class of individuals that encompasses the user (e.g., doctors, nurses, siblings, etc.). As such, the level of access provided to each requesting user corresponds to the level of permission that has been assigned to the requesting user. In other words, the requesting user can only access data in the record safe 200 that falls under a tier (or data category) that has been assigned to the requesting user. If the data access request 206 is directed to a specific data item, the request will be approved or denied based on the permission tier attached to the data item and the permission tier assigned to the requesting user.

Figure 6A:
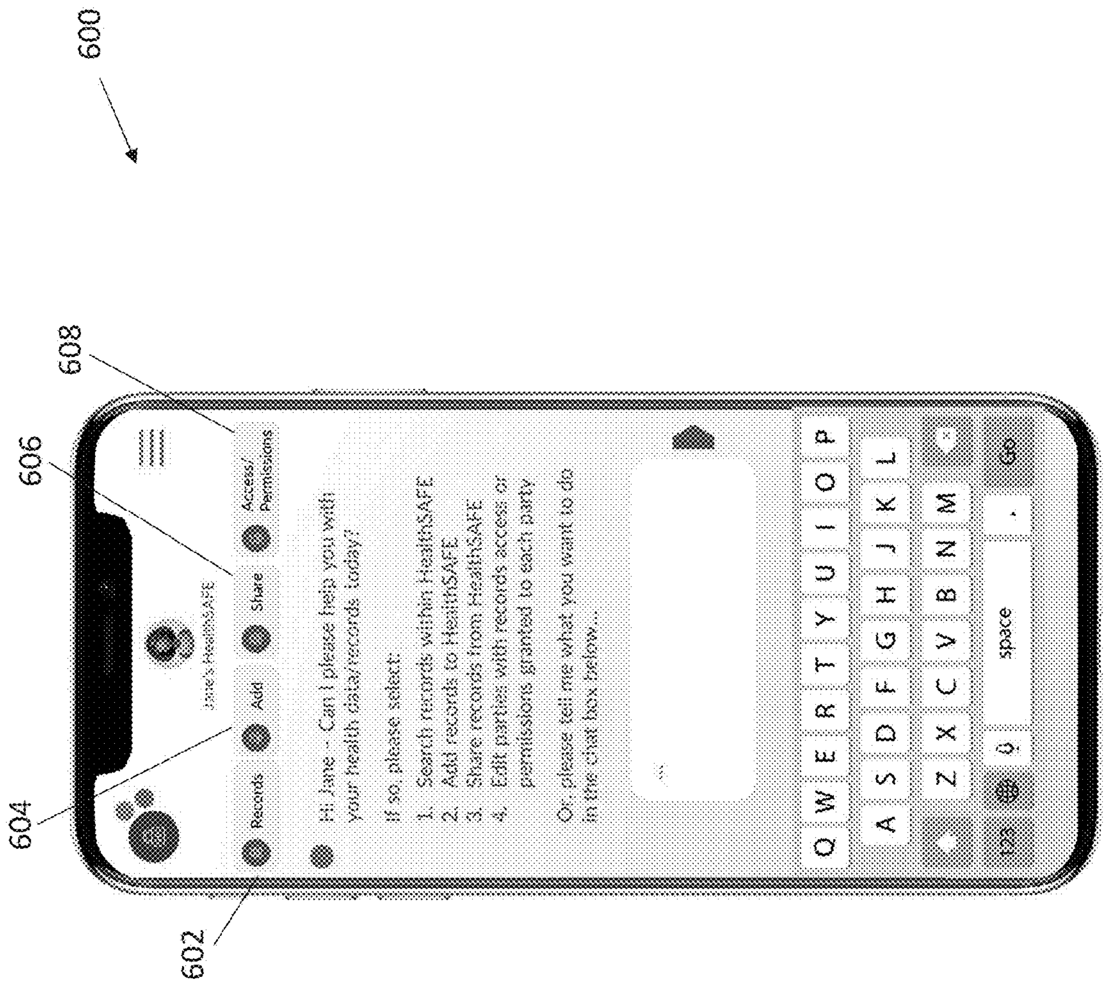
FIG. 6A is a diagram a record safe interface in accordance with aspects described herein.
Figure 6B:
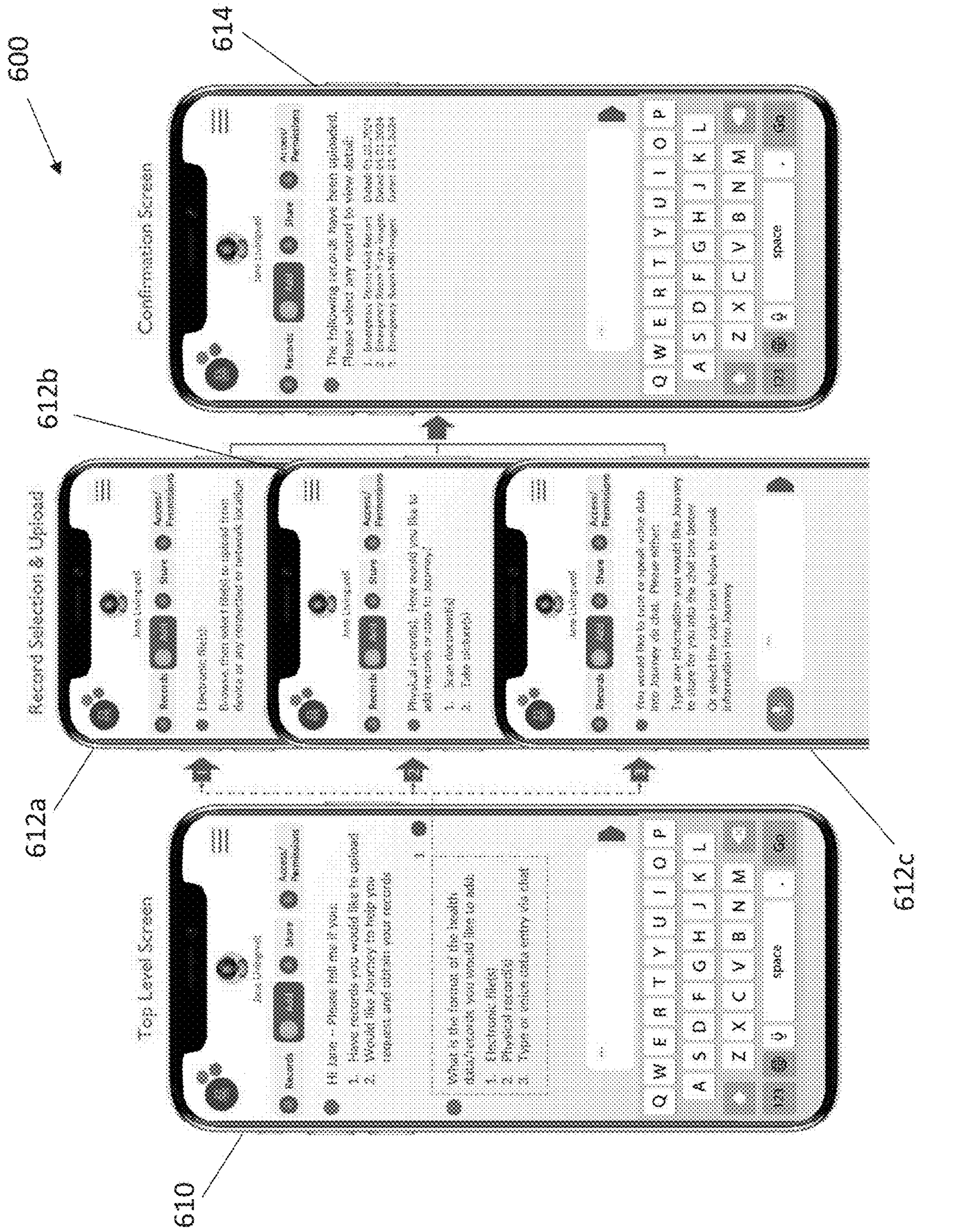
FIG. 6B is a diagram a record safe interface in accordance with aspects described herein.

FIGS. 6A and 6B illustrate examples of a UI 600 associated with a record safe in accordance with aspects described herein. In some examples, the UI 600 corresponds to a portion of the client application 118 that allows the user (e.g., the first-party user 114*a*) to access and manage the record safe 200. In some examples, the UI 600 is implemented by the safe engine 106 and the UI engine 109. As shown in FIG. 6A, the UI 600 includes a navigation tab (or series of buttons) corresponding to different safe functions. In some examples, the UI 600 includes a records tab 602 that allows the user 114 to view or otherwise access records in the record safe 200. As described above, the first-party user 114*a* may have full access to the records in their record safe 200 (or their portion/safe within the record safe 200). Likewise, third-party users 114*b*, 114*c* may select the records tab 602 to view records associated with other users, such as the records that a corresponding first-party user 114*a* has shared with the third-party user or permitted the third-party user to access. In other words, the third party users 114*b*, 114*c* will only see the records/data that have been permissioned to them.

In some examples, the UI 600 includes an add tab 604 that allows the first-party user 114*a* to add records or data. Screenshot 610 of FIG. 6B illustrates an example prompt presented to the user 114*a* after selecting the add tab 604. As shown, the user 114*a* may be asked to identify the type of data/record that they would like to add (e.g., electronic files, physical records, or typed/spoken data). Screenshot 612*a* illustrates an example prompt that is presented when the user 114*a* has indicated that they are adding electronic files. In some examples, the UI 600 enables the user 114*a* to search files/data saved on the user device 116*a*, files/data saved in a database (e.g., a cloud database), files/data saved in a medical provider record system or portal, files/data from an application associated with a device (e.g., wearable or non-wearable), or any other suitable source of electronic files/data. Screenshot 612*b* illustrates an example prompt that is presented when the user 114*a* has indicated that they are adding physical records. In some examples, the UI 600 enables the user to scan or photograph physical records to be uploaded. Screenshot 612*c* illustrates an example prompt that is presented when the user 114*a* has indicated that they are adding typed or spoken data. In some examples, the UI 600 enables the user 114*a* to enter the typed or spoken data. In some examples, the UI 600 enables the user to upload typed data from messages (e.g., text messages), emails, notes, audio recordings, voicemails, and video recordings. As shown in screenshot 614, the UI 600 may provide a confirmation prompt that shows the files/data that are being added to the record safe 200. In some examples, the UI 600 may request user confirmation before uploading the files/data to the record safe 200. It should be appreciated that the illustrations in FIGS. 6A and 6B are exemplary and are not intended to be limiting. Other types, styles, and/or configurations of UIs may be contemplated.

In some examples, the user 114*a* can provide additional information for storage in the record safe 200. For example, the user 114*a* may enter preferences for scheduling, treatment, and other categories. Such preferences may include, for example, appointment scheduling preferences, pharmacy preferences, provider and medical facility preferences, contact preferences (e.g., emergency contact lists, contacts with whom to share certain types of information), medicine preferences (e.g., Tylenol or Ibuprofen), transportation preferences, housing and/or accommodation preferences, financial preferences (e.g. payment preferences, cost-based preferences, insurance-based preferences), etc. In some examples, the additional information is automatically provisioned by the platform 100 (e.g., using API calls, AI/ML or algorithmic based logic, or other suitable means). It should be appreciated that the additional information may be assigned to tiers and/or data categories as described above. In some examples, the additional information is stored in a database (e.g., the user data database 111*b*), rather than the record safe 200.

In some examples, the user 114*a* can add insurance information for storage in the record safe 200. For example, the insurance information may include plan features, co-pay amounts, and other information. In some examples, the insurance information is automatically provisioned by the platform 100 (e.g., from an insurance provider, a medical provider, etc.). It should be appreciated that the insurance information may be assigned to tiers and/or data categories as described above. Likewise, the user 114*a* may request to share the insurance information with one or more third-party users. In some examples, the insurance information is stored in a database (e.g., the finance data database 111*e*), rather than the record safe 200.

In some examples, the user 114*a* may enter rules or preferences for automated handling of financial payments. In some examples, the finance engine 112 automatically pays bills on behalf of user 114*a* that qualify under rules/preferences set by the user 114*a*. For example, the user 114*a* may set rules that instruct the finance engine 112 to pay bills that are less than a certain amount (e.g., $50, $500, $1000, etc.). Likewise, the finance engine 112 may be configured by the user 114*a* to pay bills that come from certain medical providers or facilities. In some examples, the user 114*a* can provide payment preferences for automated payments. For example, the finance engine 112 may be configured to pay all bills using a first payment method (e.g., a credit card, an FSA card, a debit card, bank wire, ACH/EFT, PayPal. Venmo, Zelle, etc.). In some examples, the finance engine 112 is configured by the user 114*a* to use a first payment method for a first type of bill (e.g. less than $500) and a second payment method for a second type of bill (e.g., more than $500). In some examples, the finance engine 112 is configured to utilize payment plans or services (e.g., offered by banks or other consumer finance companies that may offer healthcare finance products, services or payment plans). In some examples, the finance engine 112 provides recommendations for payment methods based on the user's recent healthcare activity, insurance coverage, or other information available to the platform 100. In some examples, the financial information entered by the user 114*a* (e.g., rules and preferences) is assigned to tiers and/or data categories as described above.

In some examples, the user 114*a* can add legal documents, records, or information to the record safe 200. For example, the user 114*a* may add health care proxy documents, living wills, last wills, instructions in case of incapacity or death (e.g., for probate or non-probate matters post-death), property records, business records, or any other desired documents or information. In some examples, the legal information is automatically provisioned by the platform 100 (e.g., from a law office, government database, etc.). It should be appreciated that the legal information may be assigned to tiers and/or data categories as described above. Likewise, the user 114*a* may request to share the legal information with one or more third-party users. In some examples, the legal information is stored in a database (e.g., the user data database 111*b* or the finance data database 111*e*), rather than the record safe 200.

Figure 7:
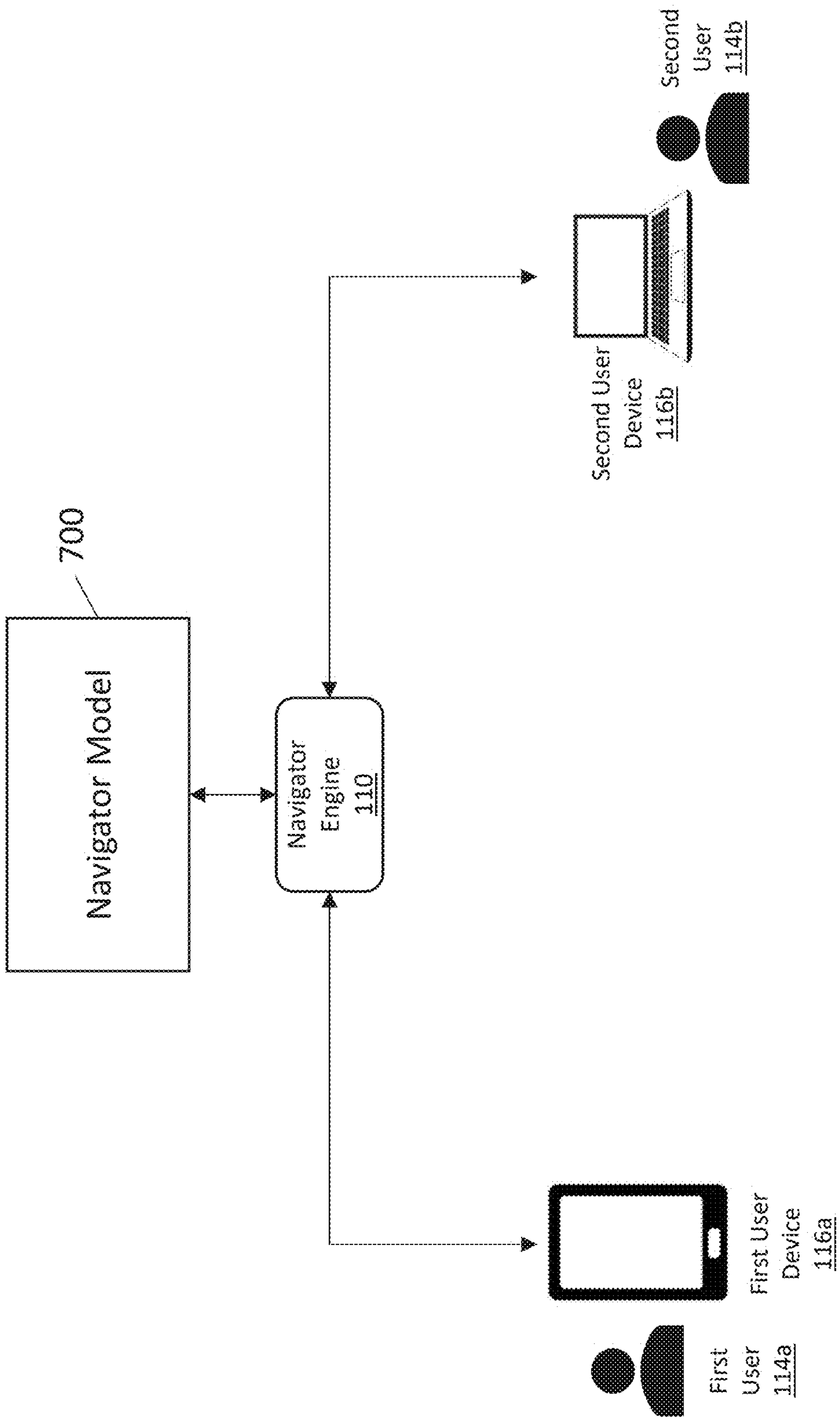
FIG. 7 is a flow diagram illustrating operation of a navigator model in accordance with aspects described herein.

In various implementations, the platform 100 can provide a health journey navigator (or agent) to guide the user 114*a* through their healthcare experience. FIG. 7 is a flow diagram illustrating operation of a navigator model 700. In some examples, the navigator model 700 includes one or more AI/ML models that are trained to guide the user 114 over the course of their healthcare and/or related or other life experiences. In some examples, the AI/ML models are trained from historical data corresponding to treatment courses for diseases and health and/or wellness conditions (e.g., cancer, HIV, infertility, etc.), as well as medical events such as heart attacks and strokes. The historical data may include treatment timelines, successes, failures, critical variables, typical questions asked by patients, recommended patient resources, recommended physician resources and more.

Figure 8A:
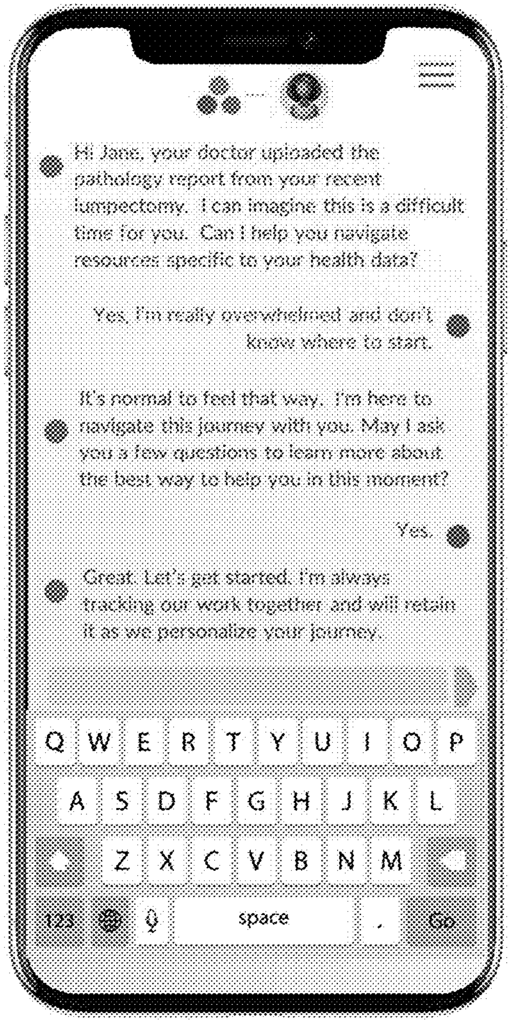
FIG. 8A is a diagram illustrating an example interaction between a navigator model and a patient in accordance with aspects described herein.
Figure 8B:
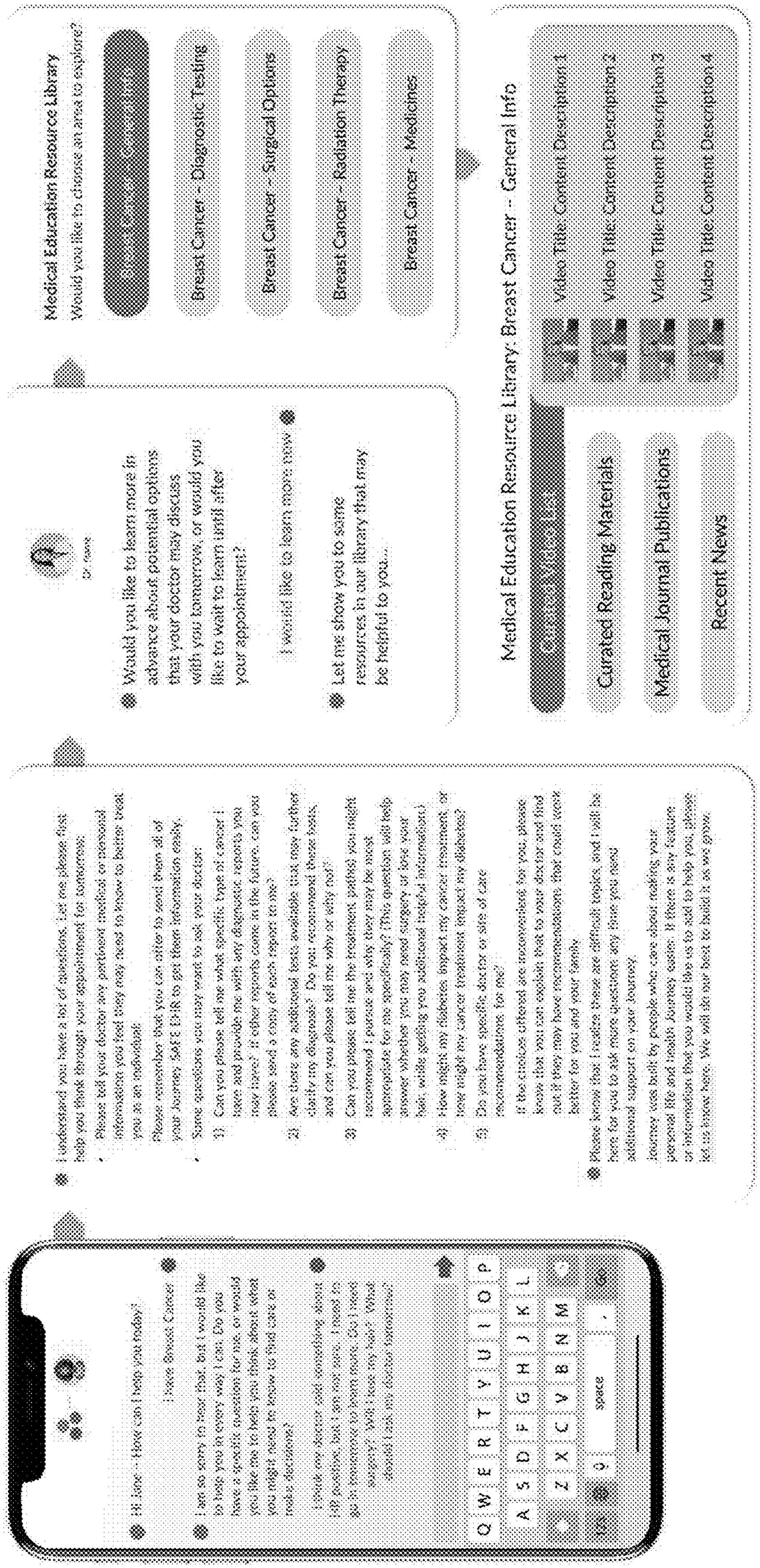
FIG. 8B is a diagram illustrating an example interaction between a navigator model and a patient in accordance with aspects described herein.

In some examples, the navigator engine 110 connects the patient (e.g., user 114*a*) and the patient's physician (i.e., user 114*b*) to the navigator model 700. The navigator model 700 learns from both the patient and the physician contributions to each individual patient's personal experience. In some examples, the navigator model 700 points users to relevant capabilities and resources based on their own preferences and the preferences or instructions of their physician. For example, the navigator model 700 can direct the user 114*a* to virtual health network tools (e.g. scheduling tools, emergency tools, patient and/or physician scribe and/or transcript tools, note-taking tools, education resources, provider and/or other care matching resources, visit preparation tools, discharge instructions and/or other discharge-related tools, medication usage tools, clinical trial related tools, nutrition tools, fitness tools, wellness tools, patient and/or physician communication tools, etc.), communities, advocacy groups and support groups based on their personal medical experiences and conditions. FIGS. 8A, 8B illustrate example interactions between the patient and the navigator model 600. In some examples, the navigator model 700 is configured to access information stored in the record safe 200 regarding the patient's preferences.

In some examples, the navigator engine 110 is configured to send notifications to the patient (i.e., user 114*a*) and/or the patient's physician (i.e., the user 114*b*). For example, the navigator engine 110 may send notifications to the users 114 via the client applications 118. Such notifications, for example, may be directed to capabilities, resources, instructions, predictions, and guidance provided by the navigator model 700. In some examples, the navigator engine 110 is configured to send notifications to family members of the patient or individuals within a patient care circle. In some examples, the patient care circle includes family, friends, physicians, doctors, care providers, or any combination thereof. In some examples, the navigator engine 110 sends notifications regarding billing dates, care planning, care management, and care ordering (e.g., prescription management, therapy appointments, etc.). In some examples, the notifications may be conditional (e.g., following the occurrence of a specific event). For example, notifications may be sent to specific individuals in the patient care circle (or the entire patient care circle) in response to an emergency event. Likewise, notifications may be sent to individuals for a specific period of time (e.g., 30 days). In such examples, the notifications may be terminated once the period of time has expired. In some examples, the notifications are based on physician preferences or settings, patient preferences or settings, or a combination of both. Such preferences may be conditional preferences (e.g., based on the occurrence of a particular event) or based on an activity sequence, as described above.

In some examples, the navigator engine 110 is configured to triage patient data to determine wait times, potential sites-of-care, and other factors. In some examples, the navigator engine 110 (or the navigator model 700) is configured to apply one or more algorithms to determine intelligent care management/guidance on behalf of physicians and medical providers. In some examples, the algorithms may correspond to specific medical providers. In some examples, the algorithms correspond to specific facilities (e.g., emergency room, urgent care, primary care, etc.). To triage patient data, the navigator engine 110 may consider user data (e.g., insurance/benefits), provider data (e.g., insurance contract information), or a combination of user, provider and/or other data available to the platform 100. In some examples, the navigator engine 110 is configured to access insurance information associated with the patient stored in record safe 200 and/or the finance data database 111*e*.

In some examples, the navigator engine 110 uses data collected from a plurality of patients to provide recommendations or referrals to individual patients. For example, a patient may indicate to the navigator engine 110 that they need a specific service (e.g., stitches, strep test, etc.). The navigator engine 110 can provide a recommended treatment location (e.g., urgent care, emergency room, etc.) based on provider factors (e.g., current demand, capabilities, etc.) and patient factors (e.g., insurance coverage). In some examples, the navigator engine 110 is configured to provide an estimated wait time for the service. In some examples, the navigator engine 110 allows the user/patient to join a waitlist at a recommended facility. Similarly, the navigator engine 110 may recommend a service, location, and/or wait time associated with a patient condition (e.g., laceration, sore throat, etc.). In some examples, the navigator engine 110 is configured to provide an estimated cost associated with the recommended or requested services. The estimated cost may be based on provider factors (e.g., insurance contract information) and patient factors (e.g., insurance coverage). In some examples, the navigator engine 110 uses insurance information stored in the record safe 200 or another database (e.g., finance data database 111*e*) to predict likely coverage determinations and/or to assist in obtaining coverage determinations and manage options for ordering prescriptions. The navigator engine 110 may use patient insurance information to identify billing and payment processes that are available for the services.

In some examples, the navigator model 700 is configured to identify or generate disease roadmaps that indicate potential disease/health condition "paths" for the user 114*a*. In some examples, the navigator model 700 suggests medical education resources based on the personal medical experiences and conditions of the user 114*a*. In some examples, the resources available to the navigator model 700 are stored in the reference data database 111*c*. In some examples, the navigator model 700 provides care matching services that assist the user 114*a* in finding diagnostic testing, new providers or second opinions, clinical trials that may be applicable to the patient, and/or insurance services that may be relevant for the patient. In some examples, the navigator model 700 is configured to integrate support communities by disease area, geography, and other patient demographics or interests. In some examples, the navigator model 700 assists the patient with intelligently navigating the patient billing experience to streamline and make the billing process easier for patients.

Figure 8C:
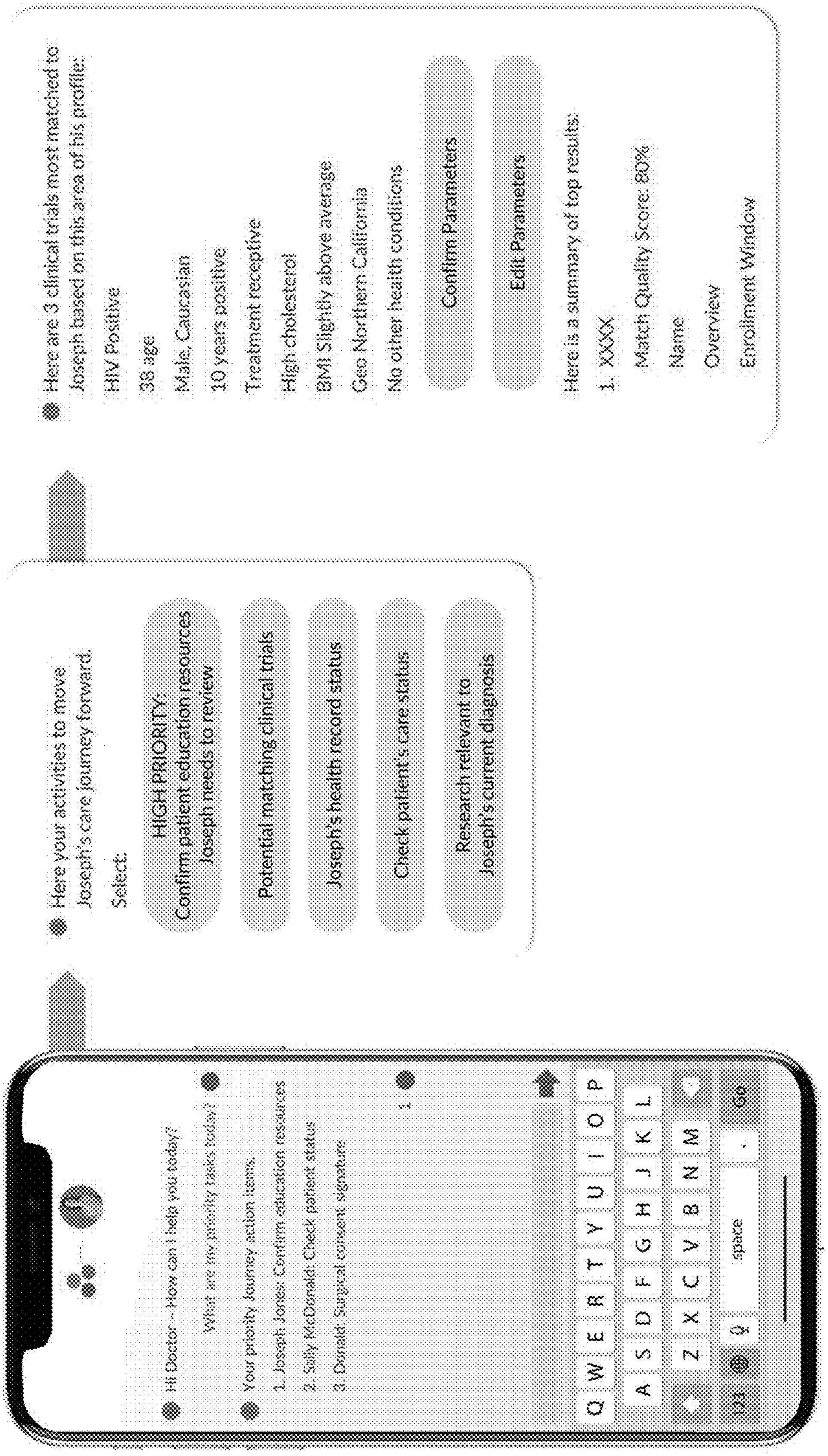
FIG. 8C is a diagram illustrating an example interaction between a navigator model and a physician in accordance with aspects described herein.

Physicians may use the navigator model 700 to review and/or to assign predicted patient and/or physician education materials and care paths for consideration. FIG. 8C illustrates an example physician interaction with the navigator model 700. In some examples, physicians can upload or assign consents or other forms that require signature to the patient through the navigator model 700 and/or the navigator engine 110. In some examples, physicians can instruct the navigator model 700 to automate and assign practice management tasks and scheduling. In some examples, the navigator model 700 serves as connection point for physicians seeking to help each other with complex diagnoses and cases to democratize access to knowledge and care that may not currently be available in all geographies or to all patients. In some examples, the navigator model 700 is configured to provide AI, ML or other algorithmically assisted requesting, including repeated follow-up requests to staff and/or reminders to patients and potentially to settle payments (e.g., stored in the medical data database 111*d* or the finance data database 111*e*).

In some examples, navigator model 700 is used to facilitate the completion of smart forms and records. In this context, a smart form or record is a digital document that streamlines data capture, documentation, and/or clinical decision making. In some cases, smart forms/records are automatically integrated with data sources and/or data sharing recipients (e.g., EHR portals). Likewise, the navigator model 700 may be used to search records and/or smart forms. The navigator engine 700 may also be used as a patient and/or physician scribe and/or note-taking companion. The navigator engine 700 may be used for smart scheduling purposes and to store/manage patient visit preparation and discharge instructions. The navigator engine 700 may be used to coordinate and/or assist patients and/or providers in the coordination of care across multiple physicians, medical facilities, service settings, diagnostic tools and/or settings, clinical trials, equipment providers, transportation services, advocacy and/or support services, etc. In some examples, the navigator model 700 manages patient and/or physician education materials and tools. In some examples, the navigator model 700 manages physician information-related templates and/or UI layouts, preferences, tools, and practice habits and preferences, all of which may utilize, be determined by, generated by or derivative of AI, ML and/or other algorithmic logic, tools and agents.

Hardware and Software Implementations

Figure 9:
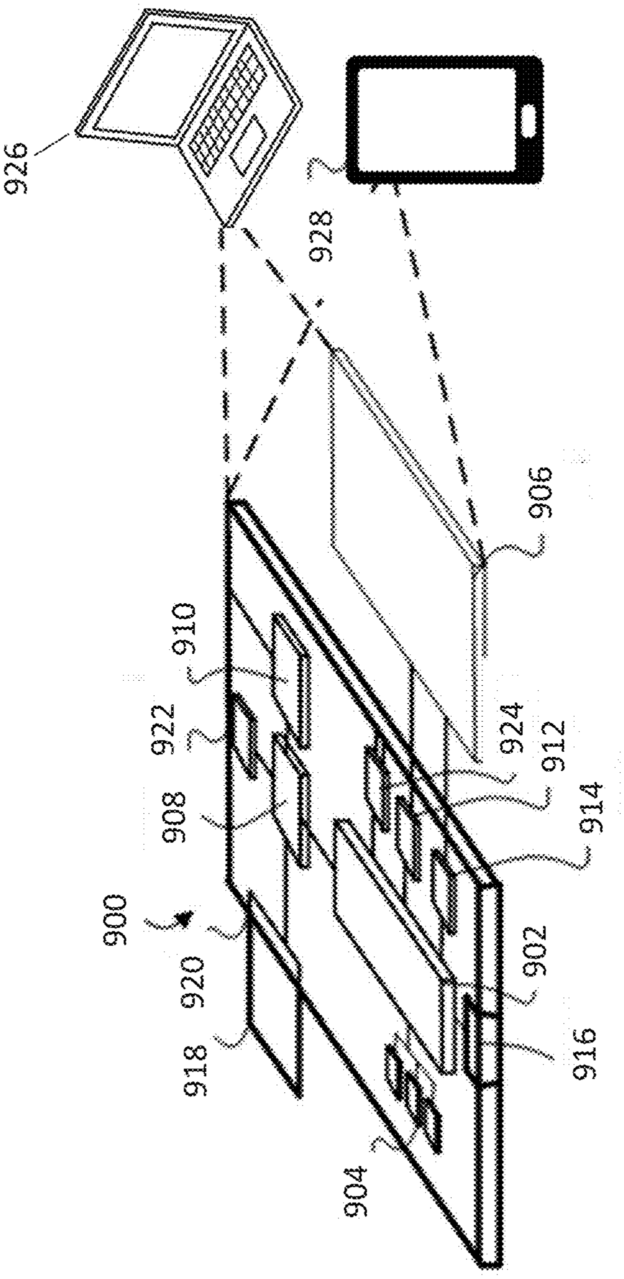
FIG. 9 illustrates an example computing device.

FIG. 9 shows an example of a generic computing device 900, which may be used with some of the techniques described in this disclosure (e.g., as user device 116 or application server 102). Computing device 900 includes a processor 902, memory 904, an input/output device such as a display 906, a communication interface 908, and a transceiver 910, among other components. The device 900 may also be provided with a storage device, such as a micro-drive or other device, to provide additional storage. Each of the components 900, 902, 904, 906, 908, and 910, are interconnected using various buses, and several of the components may be mounted on a common motherboard or in other manners as appropriate.

The processor 902 can execute instructions within the computing device 900, including instructions stored in the memory 904. The processor 902 may be implemented as a chipset of chips that include separate and multiple analog and digital processors. The processor 902 may provide, for example, for coordination of the other components of the device 900, such as control of user interfaces, applications run by device 900, and wireless communication by device 900.

Processor 902 may communicate with a user through control interface 912 and display interface 914 coupled to a display 906. The display 906 may be, for example, a TFT LCD (Thin-Film-Transistor Liquid Crystal Display) or an OLED (Organic Light Emitting Diode) display, or other appropriate display technology. The display interface 914 may comprise appropriate circuitry for driving the display 906 to present graphical and other information to a user. The control interface 912 may receive commands from a user and convert them for submission to the processor 902. In addition, an external interface 916 may be provided in communication with processor 902, so as to enable near area communication of device 900 with other devices. External interface 916 may provide, for example, for wired communication in some implementations, or for wireless communication in other implementations, and multiple interfaces may also be used.

The memory 904 stores information within the computing device 900. The memory 904 can be implemented as one or more of a computer-readable medium or media, a volatile memory unit or units, or a non-volatile memory unit or units. Expansion memory 918 may also be provided and connected to device 900 through expansion interface 920, which may include, for example, a SIMM (Single In Line Memory Module) card interface. Such expansion memory 918 may provide extra storage space for device 900, or may also store applications or other information for device 900. Specifically, expansion memory 918 may include instructions to carry out or supplement the processes described above, and may include secure information also. Thus, for example, expansion memory 918 may be provided as a security module for device 900, and may be programmed with instructions that permit secure use of device 900. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 904, expansion memory 918, memory on processor 902, or a propagated signal that may be received, for example, over transceiver 910 or external interface 916.

Device 900 may communicate wirelessly through communication interface 908, which may include digital signal processing circuitry where necessary. Communication interface 908 may in some cases be a cellular modem. Communication interface 908 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 910. In addition, short-range communication may occur, such as using a Bluetooth, WiFi, or other such transceiver (not shown). In addition, GPS (Global Positioning System) receiver module 922 may provide additional navigation- and location-related wireless data to device 900, which may be used as appropriate by applications running on device 900.

Device 900 may also communicate audibly using audio codec 924, which may receive spoken information from a user and convert it to usable digital information. Audio codec 924 may likewise generate audible sound for a user, such as through a speaker, e.g., in a handset of device 900. Such sound may include sound from voice telephone calls, may include recorded sound (e.g., voice messages, music files, etc.) and may also include sound generated by applications operating on device 900. In some examples, the device 900 includes a microphone to collect audio (e.g., speech) from a user. Likewise, the device 900 may include an input to receive a connection from an external microphone.

The computing device 900 may be implemented in a number of different forms, as shown in FIG. 9. For example, it may be implemented as a computer (e.g., laptop) 926. It may also be implemented as part of a smartphone 928, smart watch, tablet, personal digital assistant, or other similar mobile device.

Some implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language resource), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending resources to and receiving resources from a device that is used by the user; for example, by sending web pages to a web browser on a user's client device in response to requests received from the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation.

Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method for providing a virtual health platform, comprising:

receiving, from a data source, health data associated with a first user, wherein the health data is in a non-standardized format associated with the data source;

converting, by a data engine of the virtual health platform, the health data from the non-standardized format into a standardized format;

assigning at least one data category to the health data;

storing the health data in the standardized format in a database;

receiving, from a second user, a request to access the health data;

identifying a permission tier associated with the at least one data category assigned to the health data;

determining whether the second user has permission to access the health data based on the identified permission tier and an identity of the second user;

providing, by the virtual health platform, to the second user, at least a portion of the health data corresponding to data categories that the second user has permission to access, wherein health data assigned to data categories that the second user does not have permission to access is excluded from the portion provided to the second user; and automatically generating and transmitting, by the virtual health platform, a notification to at least one of the first user or a first third-party indicating that the second user has accessed the health data.

2. The method of claim 1, further comprising:

analyzing the health data to identify the at least one data category.

3. The method of claim 1, wherein the at least one data category corresponds to at least one of a data type, a data format, a data source, and a data timeframe.

4. The method of claim 1, wherein receiving the health data associated with the first user includes receiving the health data from the first user.

5. The method of claim 1, wherein receiving the health data associated with the first user includes receiving the health data from one of a medical provider, a pharmacy, a medical insurance provider, or an electronic data provider.

6. The method of claim 1, further comprising:

receiving, from the first user, an assignment of the permission tier to the at least one data category.

7. The method of claim 1, further comprising:

receiving, from the first user, a selection of one or more permission tiers that the second user is permitted to access.

8. The method of claim 1, further comprising:

determining one or more permission tiers that the second user is permitted to access based on the identity of the second user.

9. The method of claim 1, wherein receiving the request from the second user to access the health data includes receiving an indication of an event associated with the first user.

10. The method of claim 9, further comprising:

determining one or more permission tiers that the second user is permitted to access based on the identity of the second user and the event associated with the first user.

11. The method of claim 1, further comprising:

authenticating the identity of the second user.

12. A system for providing a virtual health platform, comprising:

at least one memory for storing computer-executable instructions; and at least one processor for executing the instructions stored on the at least one memory, wherein execution of the instructions programs the at least one processor to perform operations comprising:

receiving, from a data source, health data associated with a first user, wherein the health data is in a non-standardized format associated with the data source;

converting, by a data engine of the virtual health platform, the health data from the non-standardized format into a standardized format;

assigning at least one data category to the health data;

storing the health data in the standardized format in a database;

receiving, from a second user, a request to access the health data;

identifying a permission tier associated with the at least one data category assigned to the health data;

determining whether the second user has permission to access the health data based on the identified permission tier and an identity of the second user;

providing, by the virtual health platform, to the second user, at least a portion of the health data corresponding to data categories that the second user has permission to access, wherein health data assigned to data categories that the second user does not have permission to access is excluded from the portion provided to the second user; and automatically generating and transmitting, by the virtual health platform, a notification to at least one of the first user or a first third-party indicating that the second user has accessed the health data.

13. The system of claim 12, wherein execution of the instructions programs the at least one processor to perform operations further comprising:

analyzing the health data to identify the at least one data category.

14. The system of claim 13, wherein the at least one data category corresponds to at least one of a data type, a data format, a data source, and a data timeframe.

15. The system of claim 12, wherein receiving the health data associated with the first user includes receiving the health data from the first user.

16. The system of claim 12, wherein receiving the health data associated with the first user includes receiving the health data from one of a medical provider, a pharmacy, a medical insurance provider, or an electronic data provider.

17. The system of claim 12, wherein execution of the instructions programs the at least one processor to perform operations further comprising:

receiving, from the first user, an assignment of the permission tier to the at least one data category.

18. The system of claim 12, wherein execution of the instructions programs the at least one processor to perform operations further comprising:

receiving, from the first user, a selection of one or more permission tiers that the second user is permitted to access.

19. The system of claim 12, wherein execution of the instructions programs the at least one processor to perform operations further comprising:

determining one or more permission tiers that the second user is permitted to access based on the identity of the second user.

20. The system of claim 12, wherein receiving the request from the second user to access the health data includes receiving an indication of an event associated with the first user.

21. The system of claim 20, wherein execution of the instructions programs the at least one processor to perform operations further comprising:

determining one or more permission tiers that the second user is permitted to access based on the identity of the second user and the event associated with the first user.

22. The system of claim 12, wherein execution of the instructions programs the at least one processor to perform operations further comprising:

authenticating the identity of the second user.

23. The method of claim 1, further comprising:

automatically generating and transmitting, by the virtual health platform, a notification to at least one of the first user, the second user, the first third-party, or a second third-party in response to at least one of (i) receipt of the request to access the health data by the second user or (ii) a detection of an event associated with the first user.

24. The method of claim 23, wherein the event is an emergency involving the first user.

25. The system of claim 12, wherein execution of the instructions programs the at least one processor to perform operations further comprising:

automatically generating and transmitting, by the virtual health platform, a notification to at least one of the first user, the second user, the first third-party, or a second third-party in response to at least one of (i) receipt of the request to access the health data by the second user or (ii) a detection of an event associated with the first user.

26. The system of claim 25, wherein the event is an emergency involving the first user.

* * * * *